United States Patent
Han et al.

(10) Patent No.: US 12,359,158 B2
(45) Date of Patent: *Jul. 15, 2025

(54) METHODS AND SYSTEMS FOR MECHANOPORATION-BASED HIGH-THROUGHPUT PAYLOAD DELIVERY INTO BIOLOGICAL CELLS

(71) Applicant: CellFe, Inc., Alameda, CA (US)

(72) Inventors: Sewoon Han, Alameda, CA (US); Ian Sicher, Alameda, CA (US); Alexander Alexeev, Alameda, CA (US); Ockchul Kim, Alameda, CA (US)

(73) Assignee: CellFE, Inc., Alameda, CA (US)

( * ) Notice: Subject to any disclaimer, the term of this patent is extended or adjusted under 35 U.S.C. 154(b) by 101 days.

This patent is subject to a terminal disclaimer.

(21) Appl. No.: 18/456,340

(22) Filed: Aug. 25, 2023

(65) Prior Publication Data

US 2023/0416781 A1  Dec. 28, 2023

Related U.S. Application Data

(63) Continuation of application No. 18/162,372, filed on Jan. 31, 2023, now Pat. No. 11,788,050, which is a
(Continued)

(51) Int. Cl.
*C12M 1/42* (2006.01)
*C12M 1/00* (2006.01)
*C12N 15/87* (2006.01)

(52) U.S. Cl.
CPC .......... *C12M 35/04* (2013.01); *C12M 29/04* (2013.01); *C12N 15/87* (2013.01)

(58) Field of Classification Search
CPC ........ C12M 35/04; C12M 29/04; C12N 15/87
(Continued)

(56) References Cited

U.S. PATENT DOCUMENTS

| 6,544,423 B1 | 4/2003 | Baurmeister et al. |
| 8,356,714 B2 | 1/2013 | Sulchek et al. |

(Continued)

FOREIGN PATENT DOCUMENTS

| CN | 110198785 A | 9/2019 |
| CN | 117015596 B | 2/2024 |

(Continued)

OTHER PUBLICATIONS

Singapore Application Serial No. 11202303746T, Decision to Grant mailed May 20, 2024, 2 pgs.
(Continued)

*Primary Examiner* — Michael L Hobbs
*Assistant Examiner* — Lenora A Abel
(74) *Attorney, Agent, or Firm* — Polygon IP, LLP

(57) ABSTRACT

Described herein are methods and systems for mechanoporation-based high-throughput payload delivery into biological cells. For example, one system can process at least 1 billion cells per minute or at least 25 billion cells per minute, which is substantially greater than conventional methods. A cell processing apparatus comprises a processing assembly formed by stacking multiple processing components. Each processing component comprises channels, which may be used for filtration, mechanoporation, and/or separation of cells in the cell media. This functionality depends on the configuration of each channel. For example, each channel comprises one or more ridges such that each ridge forms a processing gap with an adjacent one of the processing components. The ridges may extend to the side walls or form a bypass gap with the wall. The processing gaps can be specially configured to compress cells as the cells pass through these gaps thereby initiating the mechanoporation process.

20 Claims, 20 Drawing Sheets

Related U.S. Application Data continuation of application No. PCT/US2021/059856, filed on Nov. 18, 2021.

(60) Provisional application No. 63/115,507, filed on Nov. 18, 2020.

(58) Field of Classification Search
USPC ........................................................ 435/287.2
See application file for complete search history.

(56) References Cited

U.S. PATENT DOCUMENTS

| | | | |
|---|---|---|---|
| 10,039,885 | B2 | 8/2018 | Chow et al. |
| 10,717,084 | B2 | 7/2020 | Sulchek et al. |
| 11,198,127 | B2 | 12/2021 | Sulchek et al. |
| 11,268,892 | B2 | 3/2022 | Sulchek et al. |
| 11,788,050 | B2 * | 10/2023 | Han ................ C12M 29/04 435/287.2 |
| 2007/0072290 | A1 | 3/2007 | Hvichia |
| 2011/0081674 | A1 | 4/2011 | Han et al. |
| 2011/0253224 | A1 * | 10/2011 | Linder ............ G01N 33/54313 137/2 |
| 2011/0256551 | A1 | 10/2011 | Linder et al. |
| 2014/0227777 | A1 | 8/2014 | Choi et al. |
| 2014/0273229 | A1 | 9/2014 | Meacham et al. |
| 2014/0287509 | A1 | 9/2014 | Sharei et al. |
| 2016/0193605 | A1 | 7/2016 | Sharei et al. |
| 2016/0228647 | A1 | 8/2016 | Chow et al. |
| 2016/0272961 | A1 | 9/2016 | Lee |
| 2017/0233692 | A1 | 8/2017 | Pawell |
| 2018/0003696 | A1 | 1/2018 | Sharei et al. |
| 2018/0016539 | A1 | 1/2018 | Ding et al. |
| 2018/0142198 | A1 | 5/2018 | Sharei et al. |
| 2018/0155669 | A1 | 6/2018 | Pawell |
| 2018/0201889 | A1 | 7/2018 | Sharei et al. |
| 2018/0245089 | A1 | 8/2018 | Sharei et al. |
| 2018/0327706 | A1 | 11/2018 | Qin et al. |
| 2019/0017072 | A1 | 1/2019 | Ditommaso et al. |
| 2019/0111082 | A1 | 4/2019 | Gilbert et al. |
| 2019/0177677 | A1 | 6/2019 | Jonas et al. |
| 2019/0275520 | A1 | 9/2019 | Stewart et al. |
| 2019/0322976 | A1 | 10/2019 | Williams et al. |
| 2019/0382796 | A1 | 12/2019 | Gilbert et al. |
| 2020/0172845 | A1 | 6/2020 | Baker et al. |
| 2020/0316604 | A1 * | 10/2020 | Dadgar ............ B01L 3/502776 |
| 2020/0332243 | A1 * | 10/2020 | Dadgar ................ C12M 23/42 |
| 2021/0292700 | A1 | 9/2021 | Han et al. |
| 2021/0388390 | A1 | 12/2021 | Bernstein et al. |
| 2022/0105166 | A1 | 4/2022 | Sharei et al. |
| 2022/0204908 | A1 | 6/2022 | Han et al. |
| 2022/0213422 | A1 | 7/2022 | Zamarayeva et al. |
| 2022/0298461 | A1 | 9/2022 | Zamarayeva et al. |
| 2023/0174918 | A1 | 6/2023 | Han |

FOREIGN PATENT DOCUMENTS

| | | |
|---|---|---|
| JP | 2018025759 A | 2/2018 |
| JP | 2020503847 A | 2/2020 |
| SG | 11202303746 | 7/2024 |
| WO | 2018089497 A1 | 5/2018 |
| WO | 2020026047 A1 | 2/2020 |
| WO | 2020037117 A1 | 2/2020 |
| WO | 2020210162 A1 | 10/2020 |
| WO | 2022109113 A1 | 5/2022 |

OTHER PUBLICATIONS

Williams, A.R. et al., "Filtroporation: A Simple, Reliable Technique for Transfection and Macromolecular Loading of Cells in Suspension," Biotechnology and Bioengineering, vol. 65, No. 3, Nov. 5, 1999.

U.S. Appl. No. 18/162,372, Non Final Office Action mailed Jul. 13, 2023, 30 pgs.

U.S. Appl. No. 18/162,372, Notice of Allowance mailed Aug. 24, 2023, 10 pgs.

U.S. Appl. No. 18/162,372, Restriction Requirement mailed May 25, 2023, 7 pgs.

Barber "A Technic for the Inoculation of Bacteria and Other Substances into Living Cells" The Journal of Infectious Diseases, Apr. 12, 1911, vol. 8, No. 3 (Apr. 12, 1911), pp. 348-360.

Deng et al. "Intracellular Delivery of Nanomaterials via an Inertial Microfluidic Cell Hydroporator" Nano Lett. 2018, 18, 4, 2705-2710.

Di Carlo, "Enhanced Velocity Gradients within Microfluidics for Cellular Manipulation" In: Baba, Y., Shoji, S., van den Berg, A. (eds) Micro Total Analysis Systems 2002. Springer, Dordrecht. https://doi.org/10.1007/978-94-010-0504-3_66.

DiCarlo et al. "Reagentless mechanical cell lysis by nanoscale barbs in microchannels for sample preparation" Lab on a Chip 3(4):287-91.

Ding et al. "High-throughput Nuclear Delivery and Rapid Expression of DNA via Mechanical and Electrical Cell-Membrane Disruption" Nat Biomed Eng. 2017; 1: 0039.

Hallow et al., "Shear-induced intracellular loading of cells with molecules by controlled microfluidics" Biotechnol Bioeng. Mar. 1, 2008; 99(4): 846-854. doi:10.1002/bit.21651.

Han et al. "CRISPR-Cas9 delivery to hard-to-transfect cells via membrane deformation" Science Advances Aug. 14, 2015.

International Application Serial No. PCT/US2021/059856, Search Report and Written Opinion mailed Feb. 24, 2022.

Int'l Application Serial No. PCT/US21/59856, Int'l Preliminary Report on Patentability mailed 2023-06-016 pgs.

Jarrell et al. "Intracellular delivery of mRNA to human primary T cells with microfluidic vortex shedding" Sci Rep 9, 3214 (2019).

Kang et al. "Intracellular Nanomaterial Delivery via Spiral Hydroporation" (ACS Nano 2020, 14, 3048-3058).

Liu et al "Cell mechanical and physiological behavior in the regime of rapid mechanical compressions that lead to volume change." Small 16, 1903857-11, 2020.

Liu et al "Microfluidic generation of transient cell volume exchange for convectively driven intracellular delivery of large macromolecules. Materials Today 21, 703-712, 2018".

Schmiderer et al. "Efficient and nontoxic biomolecule delivery to primary human hematopoietic stem cells using nanostraws" PNAS Sep. 1, 2020 117 (35) 21267-21273.

Sharei et al. "A vector-free microfluidic platform for intracellular delivery" Proc Natl Acad Sci U S A. Feb. 5, 2013; 110(6): 2082-2087.

Japanese Application Serial No. 2023-529914, Office Action mailed Jan. 28, 2025, 2 pgs.

* cited by examiner

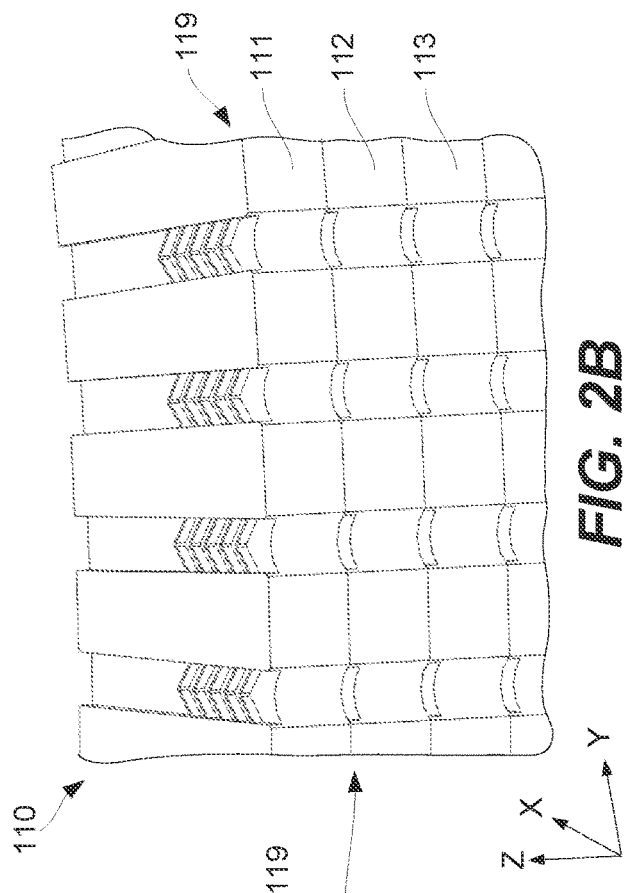
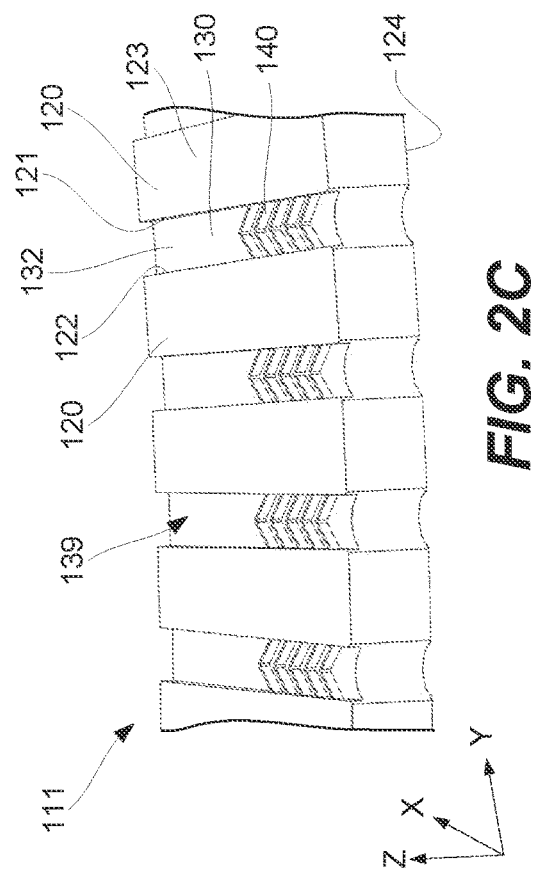
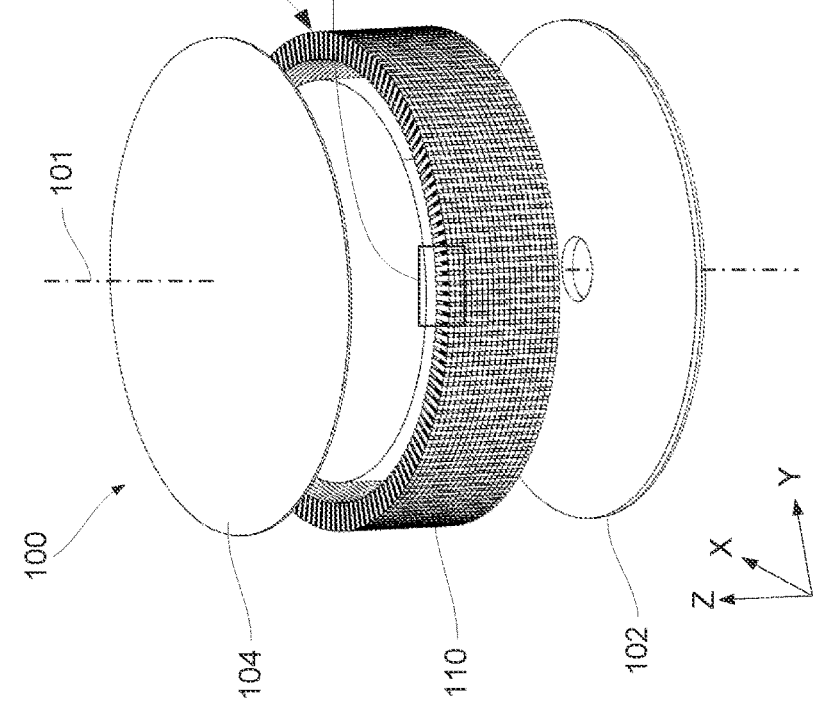
FIG. 2A
FIG. 2B
FIG. 2C

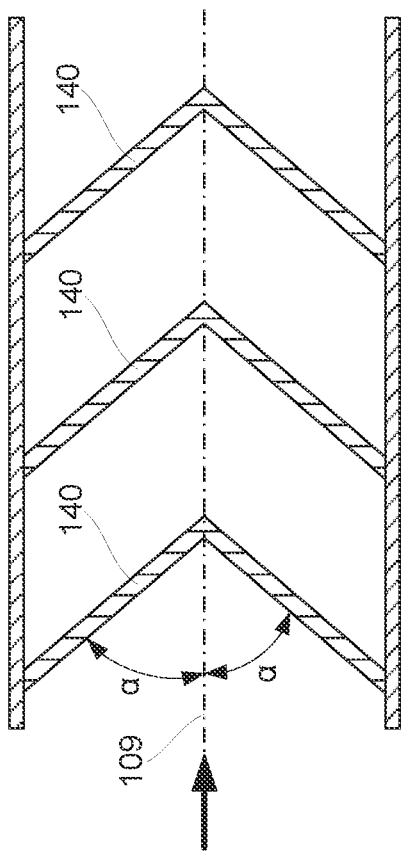
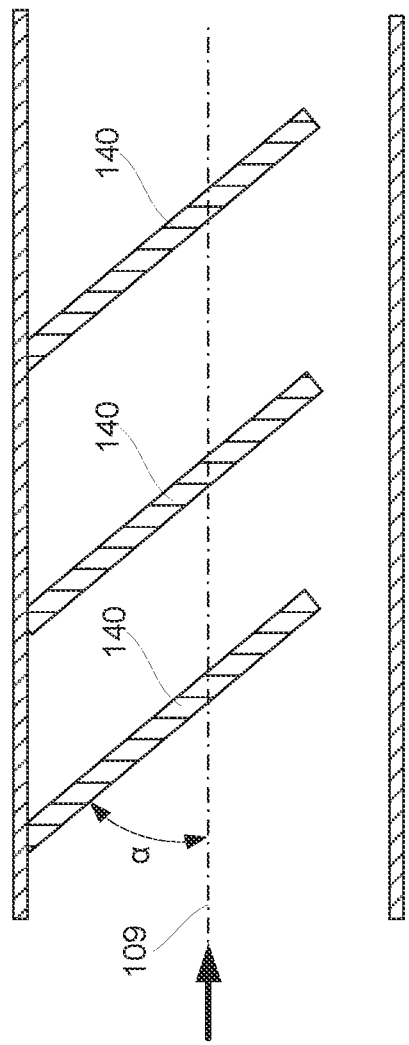
FIG. 2G
FIG. 2H

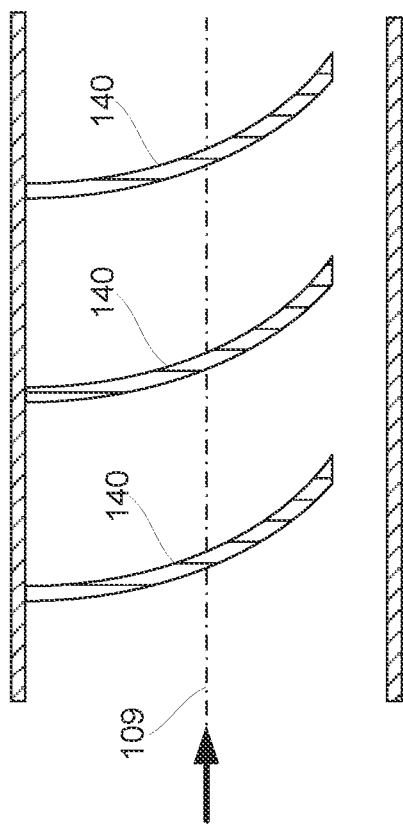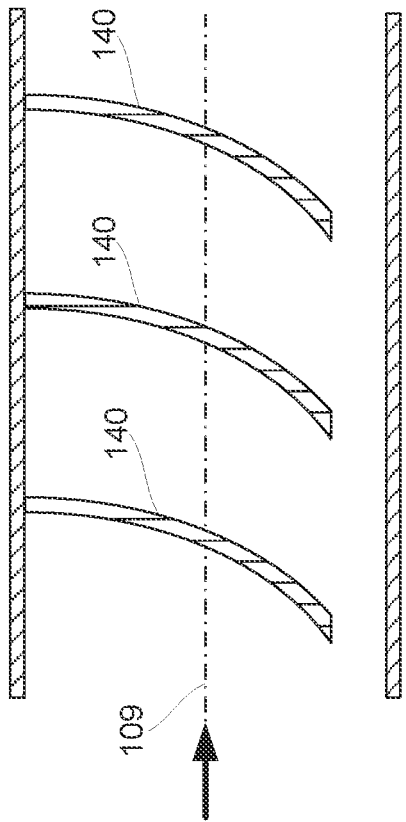

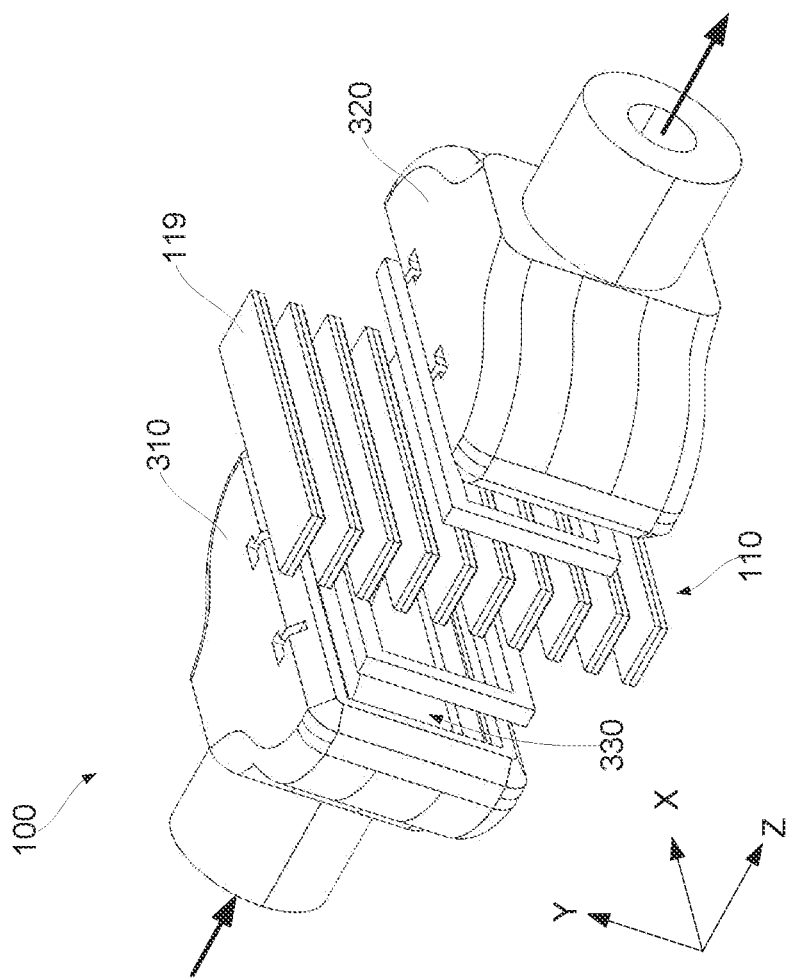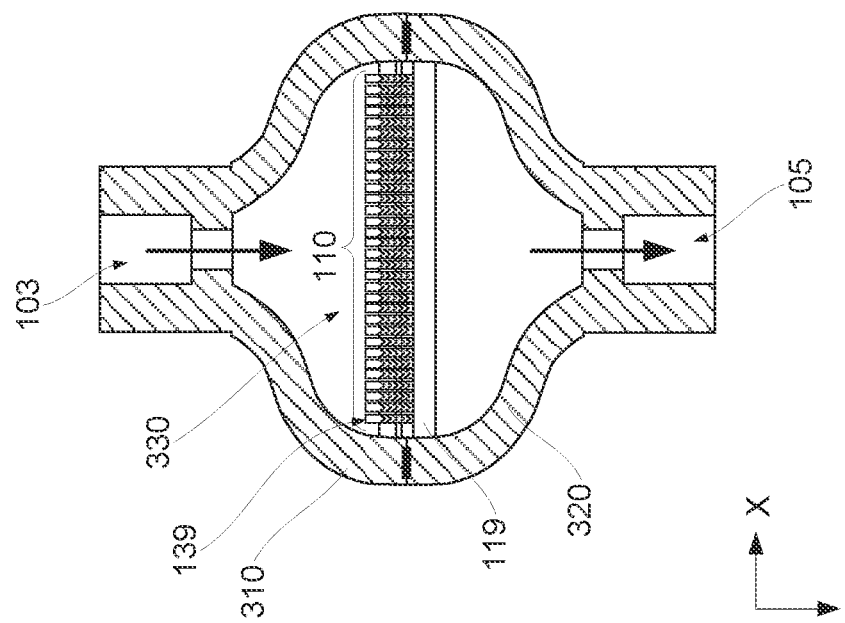
FIG. 3A
FIG. 3B

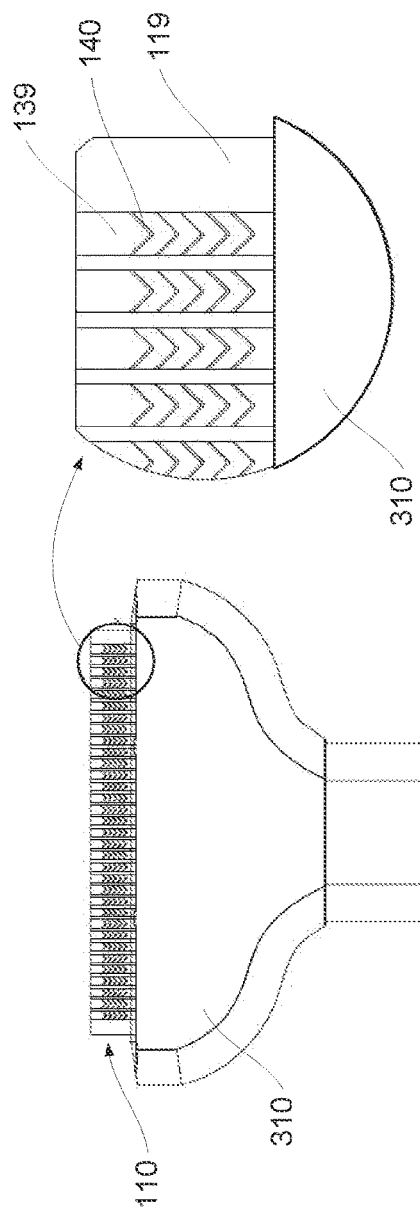
FIG. 3C
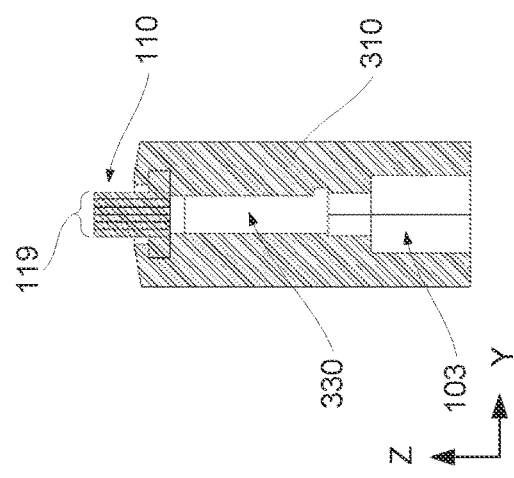
FIG. 3D
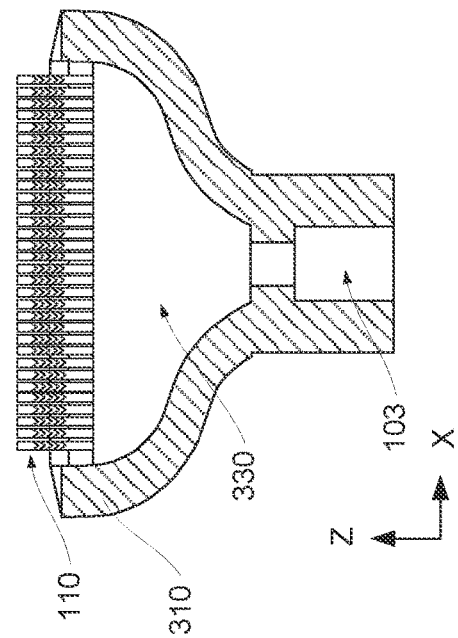
FIG. 3E
FIG. 3F

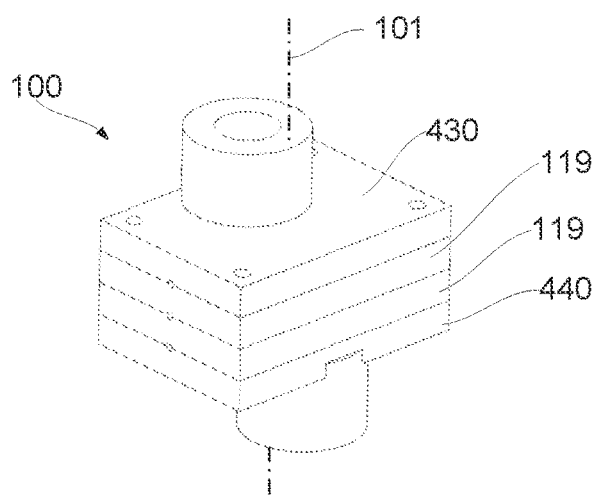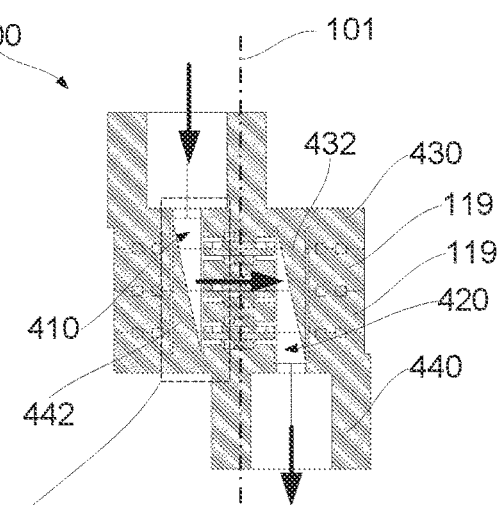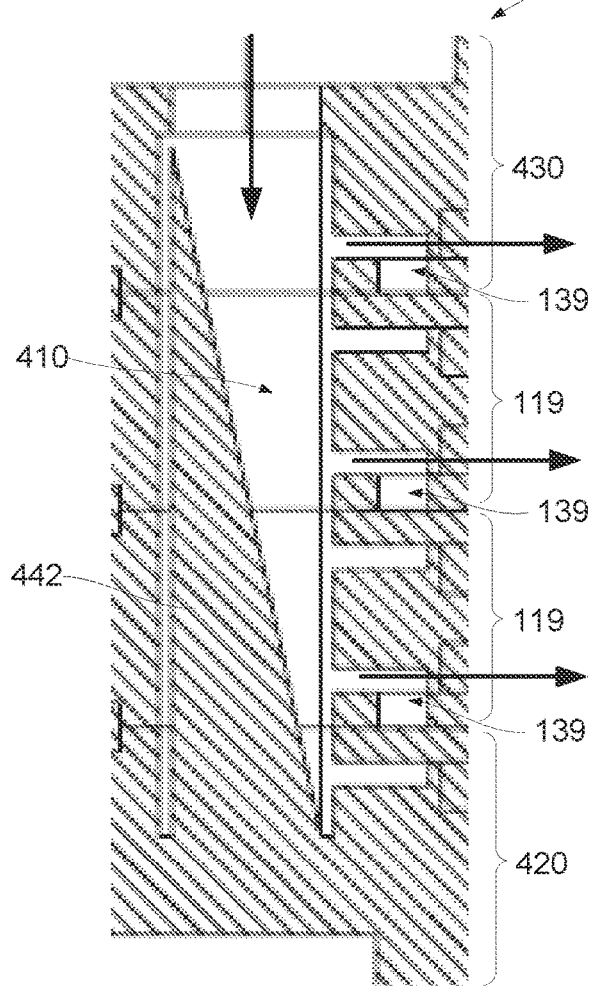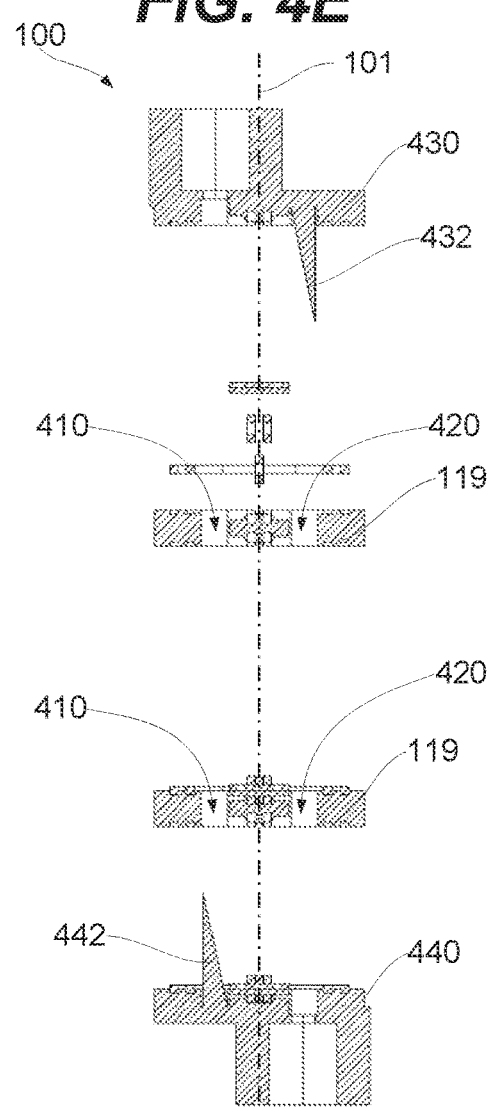
FIG. 4D
FIG. 4E
FIG. 4G
FIG. 4F

METHODS AND SYSTEMS FOR MECHANOPORATION-BASED HIGH-THROUGHPUT PAYLOAD DELIVERY INTO BIOLOGICAL CELLS

CROSS-REFERENCE TO RELATED APPLICATIONS

This application is a continuation of U.S. application Ser. No. 18/162,372, filed 2023 Jan. 31, which is a continuation of PCT Application no. PCT/US2021/059856, filed on 2021 Nov. 18, which claims the benefit under 35 U.S.C. § 119(e) of U.S. Provisional Patent Application No. 63/115,507, filed on Nov. 18, 2020, all of this which are incorporated herein by reference in their entirety for all purposes.

BACKGROUND

Intracellular delivery has many valuable applications, such as gene transfection, editing, cell labeling, and cell interrogation. However, conventional delivery methods (e.g., microinjection, electroporation, chemical poration, and sonoporation) have demonstrated low delivery efficiencies and cell viability, especially for large molecules (e.g., molecules with sizes of at least 2000 kDa) and large particles (e.g., particles with sizes of at least 50 nanometers). Furthermore, many conventional delivery methods are not able to process cells at high rates. For example, cells often require individual handling, which significantly slows down processing speeds. What is needed are new methods and systems for high-throughput payload delivery into biological cells.

SUMMARY

Described herein are methods and systems for mechanoporation-based high-throughput payload delivery into biological cells. For example, one system can process at least 1 billion cells per minute or at least 25 billion cells per minute, which is substantially greater than conventional methods. A cell processing apparatus comprises a processing assembly formed by stacking multiple processing components. Each processing component comprises channels, which may be used for filtration, mechanoporation, and/or separation of cells in the cell media. This functionality depends on the configuration of each channel. For example, each channel comprises one or more ridges such that each ridge forms a processing gap with an adjacent one of the processing components. The ridges may extend to the side walls or form a bypass gap with the wall. The processing gaps can be specially configured to compress cells as the cells pass through these gaps thereby initiating the mechanoporation process.

BRIEF DESCRIPTION OF THE DRAWINGS

FIGS. 2A, 2B, and 2C are schematic illustrations of various components of the cell processing apparatus in FIG. 1A, focusing on processing channels, in accordance with some examples.

FIGS. 2G-J are schematic top cross-sectional views of a processing channel, in accordance with some examples.

FIG. 3A is a schematic exploded view of another example of the cell processing apparatus formed by an inlet component and an outlet component, sealed to each other and enclosing a processing assembly comprising multiple processing components.

FIG. 3B is a schematic cross-sectional view of the cell processing apparatus in FIG. 3A.

FIG. 3C is a schematic top view of an inlet component of the cell processing apparatus in FIG. 3A.

FIG. 3D is an expanded top view of a portion of the inlet component in FIG. 3C, illustrating channels and ridges in a processing component.

FIGS. 3E and 3F are schematic cross-sectional views of the inlet component in FIG. 3C, illustrating a portion of the interior cavity and processing components positioned within the interior cavity, in accordance with some examples.

FIG. 4D is a schematic perspective view of another example of the cell processing apparatus with processing components stacked between an inlet plate and an outlet plate.

FIG. 4E is a schematic cross-sectional view of the cell processing apparatus in FIG. 4D.

FIG. 4F is an exploded cross-sectional view of the cell processing apparatus in FIG. 4D.

FIG. 4G is an expanded view of a portion of the cell processing apparatus in FIG. 4E, illustrating an outlet protrusion extending into the inlet opening of each processing component and occupying different volumes in the outlet opening of each different processing component.

DETAILED DESCRIPTION

Figure 1B:
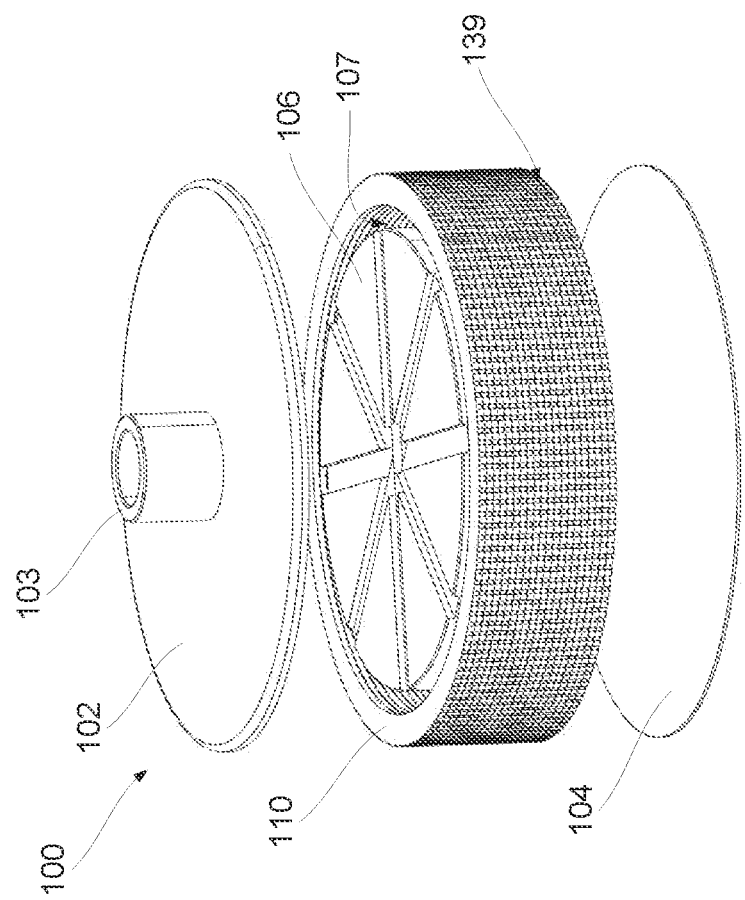
FIG. 1B is a schematic exploded view of the cell processing apparatus in FIG. 1A, in accordance with some examples.

In the following description, numerous specific details are outlined to provide a thorough understanding of the present invention. The present invention may be practiced without some or all of these specific details. In other instances, well-known process operations have not been described in detail to avoid obscuring the present invention. While the invention will be described in conjunction with the specific examples, it will be understood that it is not intended to limit the invention to the examples.

Introduction

Microfluidic techniques provide new opportunities for processing and manipulation of biological cells, such as the delivery of payload into cells for gene engineering and other applications. For purposes of this disclosure, a "microfluidic" technique is defined as a process of passing fluid through a channel, which has the smallest dimension of less than 1 millimeter. For example, an apparatus may include one or more constrictions forming a gap that is less than 1 millimeter.

A specific example of a microfluidic technique is mechanoporation, which involves mechanical actions on cells to deliver a payload into the cells. For example, cells are passed through narrow gaps (which may be also referred to as constrictions). The gaps are formed by ridges, e.g., extending from one wall toward another wall. The ridges (and as a result the gaps) can have specific geometry (e.g., sharp ridge). Furthermore, cells can be flown at certain processing conditions (e.g., high linear flow rates). Various combinations of these structural and processing conditions can cause rapid cell compression resulting in some cell volume losses. When the cells pass each constriction and are allowed to recover, the cells return to the original volume by absorbing surrounding media, which comprises a payload. As such, a combination of the volume loss followed by the volume gain results in a very efficient payload transfer into the cells. This payload transfer can be referred to as a convective delivery to differentiate from, e.g., diffusion-based delivery during which the payload is driven through the cell membranes by the concentration gradient. However, the diffusion-based delivery takes a long time and is limited to small-sized payloads. Mechanoporation provides substantially faster transfers and is less impacted by the payload size.

The cell compression is achieved in flow channels, each comprising one or more ridges. As noted above, each ridge forms a gap, with the gap size (G) being smaller than the cell diameter (D), at least for cells in a relaxed state/non-compressed state. A combination of the gap size, ridge geometry, and the linear flow rate causes cell compression and volume loss. The mechanoporation with volume change should be distinguished from other microfluidic techniques, which are not based on volume changes and one of which is briefly mentioned above. For example, other microfluidic techniques (e.g., membrane shearing) involve changing the porosity of cell membranes, thereby enabling diffusion-based payload delivery. More specifically, membrane shearing does not involve rapid compression and volume changes. Instead, the cells are passed through tapered funnels that form full circumferential contact with the cell membranes. This full circumferential contact ensures that a large portion of the cell membranes experiences shearing, resulting in the membrane poration with pores sufficiently large for payload diffusion in the cell interior.

One aspect of microfluidic techniques is the small size of flow channels, resulting in flow conditions represented by low Reynolds numbers (e.g., less than 1). As such, fluid viscosity is a dominant factor in these flow conditions. Furthermore, the overall throughput of a single channel is limited. For example, a volumetric flow rate of a single channel having a width of 1 millimeter can be less than 1 ml/min. This flow rate corresponds to the processing speed of about $10^7$ cells per hour. At the same time, industrial applications require much larger processing speeds, such as $10^9$ or $10^{10}$ cells per hour, which has significantly limited the adoption of microfluidic techniques in the past.

Furthermore, processing speeds should be maintained at or close to set values despite all possible process and material variations. For example, cell media often contains unwanted particles, abnormal cells, and other such components, which are not able to pass through microchannels, especially through gaps formed by ridges within the channels. Such media components can accumulate in some channels and even block the flow through the channels, thereby reducing the throughput capacity of the overall device.

Different approaches are available to increase the processing speed of a channel. For example, cell concentration in provided cell media, which flows through the channel, can be increased. However, higher cell concentrations (e.g., greater than 10 million cells/mL) can lead to undesirable cell-to-cell collisions. These cell-to-cell collisions can damage the cells thereby reducing cell recovery and viability. Furthermore, these collisions may cause channel clogging, resulting in reduced processed speed.

Another approach is increasing the linear flow speed by increasing the pressure differential across the channel. For example, a linear speed of 1 m/s may require a pressure differential as high as $10^6$ Pa in some channels. Such high-pressure differentials require complex and expensive equipment. Furthermore, high flow speed can be damaging to cells.

Another approach for increasing the processing speed involves using multiple parallel channels. This approach produces a proportional increase in the volumetric flow rate without requiring an increase in linear flow speeds/pressure differentials, cell concentrations, and other like methods. However, this multi-channel approach requires special considerations for maintaining the same or similar conditions in all channels, operating in parallel. Maintaining this processing condition uniformity can be challenging. For example, all channels need to have similar linear flow rates of the media, cell concentrations in the media, payload concentrations in the media, and the like. Furthermore, these conditions have to be maintained across multiple processing runs/different batches.

Described herein are methods and systems for mechanoporation-based high-throughput payload delivery into populations of biological cells, which address various challenges described above. Specifically, a cell processing apparatus includes a processing assembly, which can be replaceable and/or disposable in some examples. At least individual components of the processing assembly can be easily replaced, e.g., after processing, which in some instances can cause partial clogging of channels. For example, a pressure differential (for a given volumetric flow) is measured across the processing assembly and the entire processing assembly or some components of the assembly are replaced when this pressure differential reaches or exceeds a certain threshold. Furthermore, components of the processing assembly can be replaced to form different configurations of the processing assembly, e.g., different mechanoporation characteristics. Finally, individual components are easy to manufacture, e.g., using injection molding.

Cell Processing Apparatus Examples

Figure 1A:
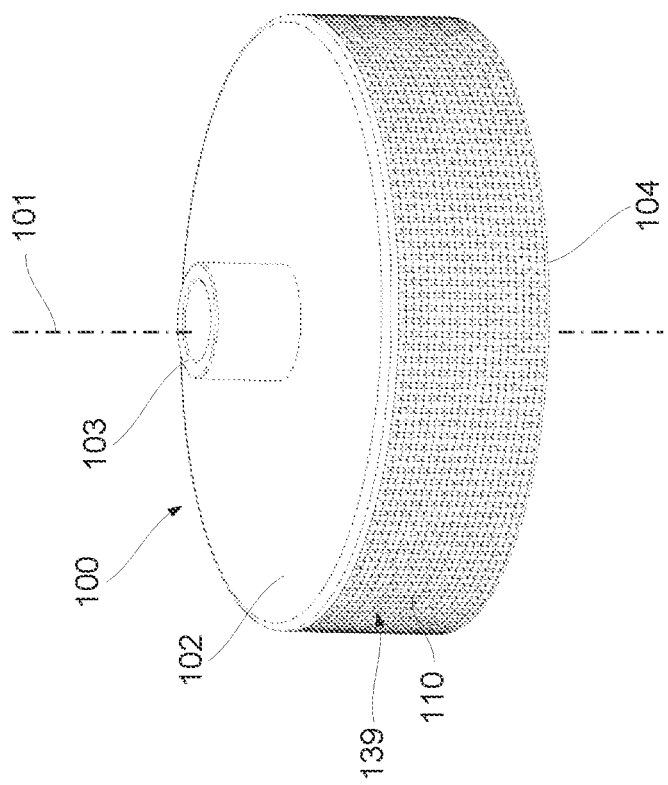
FIG. 1A is a schematic perspective view of a cell processing apparatus, in accordance with some examples.

FIG. 1A and FIG. 1B are schematic representations of cell processing apparatus 100 (in an assembled form and exploded view), in accordance with some examples. Cell processing apparatus 100 comprises processing assembly 110, inlet component 102, and stopper 104. Processing assembly 110 is disposed between inlet component 102 and stopper 104. More specifically, each inlet component 102 and stopper 104 is sealed against processing assembly 110. Collectively, processing assembly 110, inlet component 102, and stopper 104 define and enclose cavity 107 of cell processing apparatus 100. Cavity 107 can be also referred to as an inlet opening. In some examples, cell processing apparatus 100 also comprises distribution component 106, positioned inside cavity 107.

Referring to FIG. 1A and FIG. 1B, inlet component 102 comprises inlet 103 providing fluidic access to cavity 107. During the operation of cell processing apparatus 100, cell media containing a population of cells is delivered through inlet 103 into cavity 107. Distribution component 106 then uniformly distributes the cell media to different portions of cavity 107 and toward processing assembly 110.

Processing assembly 110 comprises multiple channels 139, which allow the cell media to pass through processing assembly 110 while being subjected to the mechanoporation in each channel. In some examples, processing assembly 110 comprises at least about 100 channels, at least about 500 channels, or even at least about 1000 channels. Referring to the example in FIG. 1A and FIG. 1B, each channel 139 extends radially from primary axis 101 of cell processing apparatus 100 through processing assembly 110. However, other examples (e.g., when channels 139 extend parallel to each other) are also within scope.

FIG. 2A is another schematic representation of cell processing apparatus 100, from a different angle that may be referred to as a bottom perspective view. In this example, stopper 104 does not include any outlets. Instead, an outlet may be provided in an enclosure (not shown in FIGS. 1A, 1B, and 2A). Various examples of inlets and outlets are further described below.

FIG. 2B is an expanded view of processing assembly 110 in FIG. 2A, showing processing components 119, forming processing assembly 110. For example, processing components 119 are stacked together along primary axis 101 of cell processing apparatus 100 (in the Z-direction). In this example, primary axis 101 may be also referred to as a center axis. Specifically, processing components 119 are shaped as rings with primary axis 101 extending through the centers of these rings.

More specifically, FIG. 2B illustrates processing component 111, second processing component 112, and third processing component 113, stacked together along the Z-axis. Processing components 119 may include any number of processing components (e.g., one, two, three, four, five, or more). This number depends on the desired processing speed/processing throughput of cell processing apparatus 100 as further described below. It should be noted that a larger number of processing components 119 also allows using cell processing apparatus 100 for a longer duration. Specifically, the channels of these processing components 119 can get clogged over time. A larger number of processing components 119 corresponds to a larger number of channels, which would take longer to clog (e.g., cell processing apparatus 100 at a reduced capacity can continue to operate as the channels continue to clog). However, increasing the number of processing components 119 can present various challenges for the uniform distribution of the cell media to each channel. As noted above, each channel needs to process cells in substantially the same manner, e.g., at the same flow rate, pressure, media concentration, and the like.

Referring to FIG. 2C, processing component 111 comprises channels 139. Each processing component 111 may include any number of channels. Similar to the number of processing components, this channel number depends on the desired processing speed/throughput of cell processing apparatus 100. Therefore, the overall processing throughput of cell processing apparatus 100 depends on the throughput of each channel, the number of channels in each processing component, and the number of processing components in the apparatus (as shown by the following formula):

Apparatus Throughput=Channel Throughput×Channels per Component×No of Components

In some examples, each of processing components 119 has the same design, e.g., to ensure processing consistency and interoperability. For example, processing components 119 may be supplied as consumables and assembled into processing component 111 before the use of cell processing apparatus 100.

In some examples, each processing component 119 is fabricated individually, e.g., using injection molding and/or thermal embossment. An injection molding tool can be formed by CNC machining and/or nickel plating (e.g., the tool portions used to form ridges 140). Unlike other components of processing components 119, ridges 140 have many small features that require significant precision.

Figure 2D:
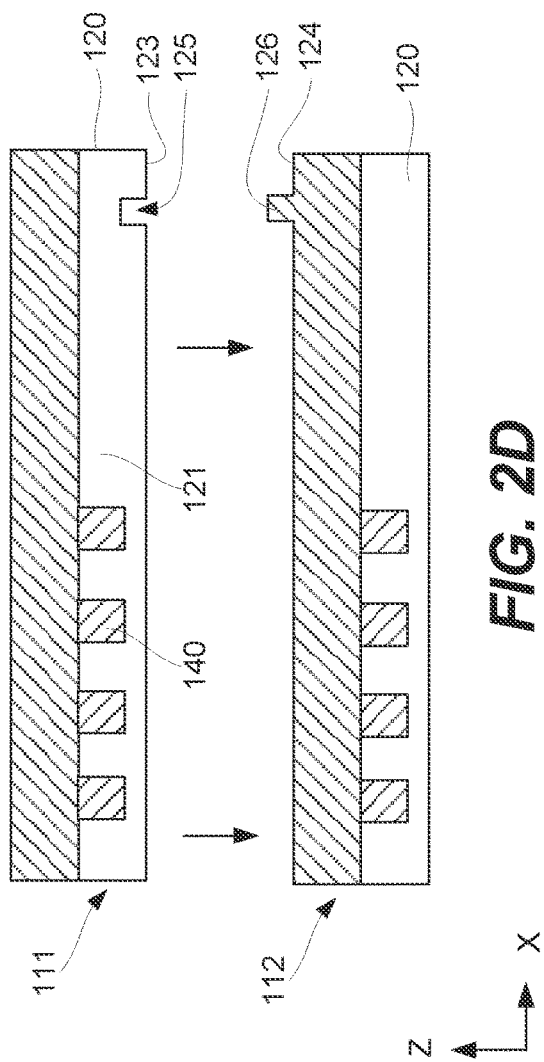
FIGS. 2D and 2E are schematic illustrations of two processing components before and after stacking, to form a processing assembly, in accordance with some examples.
Figure 2E:
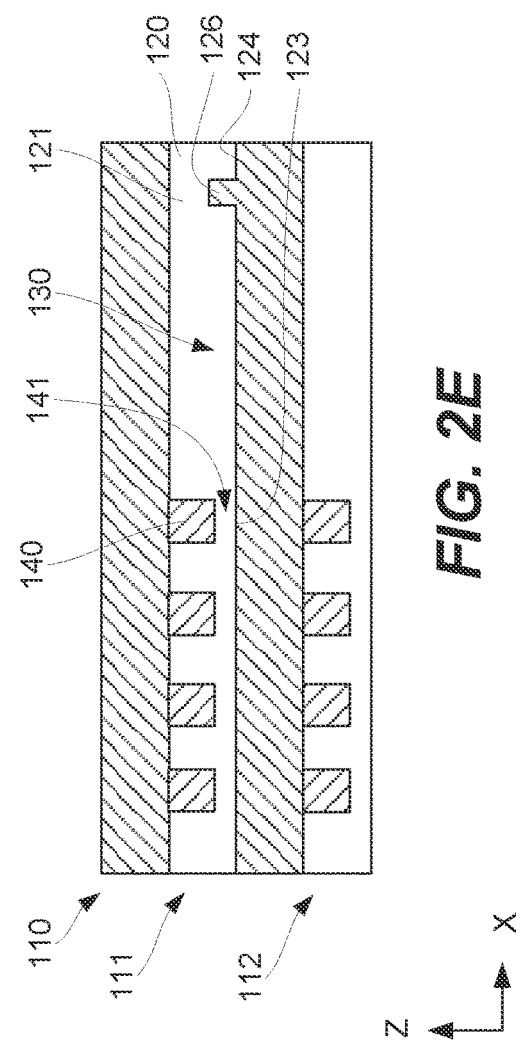
Figure 2F:
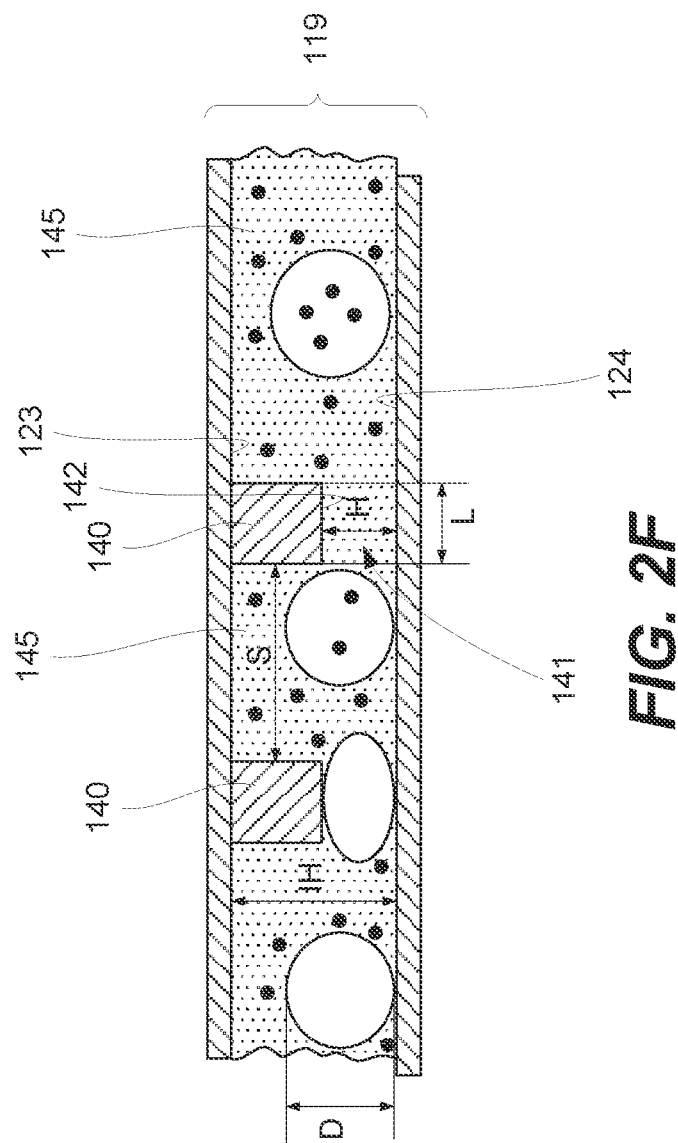
FIG. 2F is a schematic side cross-sectional view of a processing channel, in accordance with some examples.

Before stacking these processing components 119, each processing component 119 comprises an open channel with ridges 140 positioned on the bottom of the channel and extending toward the opening. Once this processing component 119 is stacked with another processing component 119, the channel is closed and ridges 140 facing his other processing component 119 that form a gap with each of these ridges 140. In some examples, each processing component 119 comprises all channel walls as, e.g., is schematically shown in FIG. 2F. For example, each of processing components 119 can be formed from two portions that are bonded together to form enclosed channels 130. These processing components 119 can be stacked together to form cell processing apparatus 100. In some examples, individually formed processing components 119, each comprising multiple enclosed channels can be used to improve the uniformity of channel dimensions. The material used for channels 139 may be a thermal plastic, such as cyclic olefin copolymers (COC), cyclic olefin polymers (COP), polymethyl methacrylate (PMMA), polyethylene terephthalate (PET), and polystyrene (PS). Furthermore, non-thermoplastic materials like glass, silicon, metals, and the like, may be used.

In some examples, two adjacent processing components 119 are bonded together using different methods, such as thermal bonding, adhesive bonding, solvent bonding, ultrasound bonding, laser welding, pressure-sensitive adhesive, and ultraviolet (UV) glue. Furthermore, in some examples, a seal is formed between two adjacent processing components 119 to prevent cell media from flowing between these components. The seal may be formed in addition or instead of bonding the components. In some examples, the seal is formed by bonding. In some examples, the seal is formed by a gasket. One example of the seal is shown in FIGS. 2D and 2E. Specifically, processing component 111 comprises sealing channel 125 while second processing component 112 comprises sealing protrusion 126. When processing component 111 is stacked with second processing component 112, sealing protrusion 126 is inserted into sealing channel 125 forming a seal. It should be noted that each of sealing protrusion 126 and sealing channel 125 (as well as the seal formed by these components) is circumferentially closed. FIG. 2B illustrates an example where two adjacent ones of processing components 119 directly interface with each other, without any intermediate components.

Examples of Mechanoporation Features Positioned in Each Channel

Referring to FIG. 2C, each channel 130 comprises one or more ridges 140. Each one of these ridges 140 is configured to compress cells as the cells pass through a gap formed by this ridge. In some examples, ridges 140 are configured to simultaneously compress multiple cells distributed along the ridge length, such as from 1 cell to 100 cells, or more than 100 cells. In other words, multiple cells can be compressed by the same since the length of the ridge is much greater than the diameter of the ridge. As such, the number of ridges 140 in each channel 130 depends on the number of compressions needed during each pass through cell processing apparatus 100. In some examples, the number of ridges 140 in each channel 130 is 1 to 50 or, more specifically, 2 to 20 such as 5 to 15. In some examples, the number of ridges in each channel 130 is the same for all channels of cell processing apparatus 100. In some examples, the overall length of each channel 130 between about 0.05 millimeters to 100 millimeters, or more specifically, between about 1 millimeter and 10 millimeters. Shorter channel lengths are beneficial for reducing the pressure required to produce desired flow speed. In some examples, ridges 140 are distributed uniformly along the channel length. Alternatively, ridges 140 can be clustered closer to the channel outlet, e.g., to enable cell focusing prior to the cell interaction with ridges 140. In some examples, ridges 140 are clustered closer to the channel inlet, e.g., to allow longer time for cells to remain in the fluid with higher speed after interactions with ridges 140. In some examples, the channel inlet and/or the channel outlet are located at the front and back edges of processing components 119. In some examples, the channel inlet and/or outlet can be arranged through channel wall 132 of processing component 119, e.g., to reduce the amount of dust entering each channel 130 due to the fabrication process.

Furthermore referring to FIG. 2C, each channel 130 is positioned between two dividers 120. In some examples, the width of divider 120 is from 1 micrometer to 100 micrometers, or from 0.1 mm to 0.5 mm, or from 0.5 mm to 10 mm. Furthermore, each channel 130 is defined by first divider wall 121, second divider wall 122, and channel wall 132. Ridges 140 protrude from channel wall 132 and may extend between and first divider wall 121 and second divider wall 122. However, the height of ridges 140 is smaller than the height of first divider wall 121 and second divider wall 122. In some examples, the height of first divider wall 121 is the same as the height of second divider wall 122. In some examples, the height of the divider 120 is from 1 micrometer to 50 micrometers, or from 20 micrometers to 500 micrometers, or from 0.1 millimeters to 10 millimeters, or more than 10 millimeters. The channel width in the Y direction defines the number of cells that are processed by compressive ridges 140 simultaneously. Wider channels allow for a larger amount of cells to be compressed in parallel. Wider channels, however, are more likely to deform (e.g., under the internal pressure within the channels) affecting the uniformity of the gap formed by ridges 140. Narrow channels, on the other hand, are more prone to clogging. In some examples, the channel width is from about 10 micrometers to about 1 millimeter, or more specifically from about 0.1 millimeters to 0.5 millimeters, or from about 0.4 millimeters to 0.8 millimeters. In some examples, the channel width is from about 1 millimeter to about 10 millimeters, or wider than 5 millimeters.

FIG. 2D illustrates a side cross-sectional view of processing component 111 and second processing component 112, prior to stacking these components. Processing component 111 comprises first surface 123, formed by divider 120, and facing second processing component 112. Second processing component 112 comprises second surface 124, facing away from divider 120 of this component and facing first processing component 111.

FIG. 2E illustrates a side cross-sectional view of processing component 111 and second processing component 112, after stacking these components/after forming processing assembly 110. At this stage, first surface 123 of processing component 111 contacts second surface 124 of second processing component 112, thereby isolating adjacent channels 130. In some examples, first surface 123 is bonded and/or sealed to second surface 124. The height of these channels (in the Z-direction) is defined by the height of the divider walls (e.g., first divider wall 121 shown in FIG. 2D). Because ridges 140 are shorter than the divider walls, ridges 140 of processing components 111 form gaps 141 with second surface 124 of second processing component 112. These gaps 141 are specifically configured to compress cells as these cells pass through each of gaps 141 and cause the volumetric change in each cell. Additional gap features will now be described with reference to FIG. 2F.

Referring to FIG. 2F, each gap 141 is identified with a corresponding height, labeled as "H". The gap height is selected such that cells are compressed to pass through gap 141. In other words, the gap height is smaller than the cell size (H<D). It should be noted that FIG. 2F illustrates an example in which the cross-sectional profile of ridge 140 is rectangular. However, other shapes of the profile are also within the scope, e.g., cylindrical, trapezoidal, or triangular. In some embodiments, the plurality of compressive surfaces may be orthogonal.

Another characterization, at least of rectangular ridges 140, is the length of ridge surface 142 in the X direction (identified as "L"), which may be also referred to as the ridge thickness. In some examples, the ridge surface length is between about 1 micrometer and 100 microns or, more specifically between about 20 micrometers and 50 micrometers. This length, together with the linear flow rate, defines the period during which a cell is compressed by the ridge. In some examples, ridge surface 142 is parallel to second surface 124. In other words, gap 141 is defined by two parallel surfaces. These parallel compressive surfaces allow for a uniform compression for the entire cell. Additionally, the compression surfaces can be converging and/or diverging. It should be noted that in addition to the cell compression, ridges 140 also produce hydrodynamic mixing within the cell media Referring to FIG. 2F, gap 141 is selected based on the cell size, compression needed, and other characteristics of mechanoporation. In some examples, the gap height (H) is between 1 micrometer and 20 micrometers, or between 10 micrometers and 100 micrometers or, more specifically, between 3 micrometers and 8 micrometers. Furthermore, the gap height (H) may be also defined relative to the cell size (D), which is defined as the average largest cross-sectional dimension of cells. More specifically, the ratio of the gap height to the cell size (H/D) defines cell compression. In some examples, this H/D ratio is between 25% and 75% or, more specifically, between 30% and 60%. Internal channel height (IH) defines the flow speed between ridges and the time that the cell spends between consecutive compressions. In some examples, the IH is between about 2 micrometers and 100 micrometers or more specifically between 5 micrometers and 10 micrometers or between 10 micrometers and 15 micrometers. In some examples, IH is between about 10 micrometers and 1 mm or more specifically between 50 micrometers and 100 micrometers.

The gap height (H) may be the same for all ridges 140 in the same channel. Alternatively and with reference to FIG. 2F, the gap height (H) may be different for different ridges 140. For example, the gap height decreases along the direction of the flow thereby subjecting the cells to higher compression as the cells flow through cell processing apparatus 100. In some examples, when larger cells are compressed in larger gaps, these cells may retain a flattened (pancake-like) shape and can then pass through smaller gaps, again without being removed from the flow. This feature may be referred to as a staged-compression. Furthermore, the smaller gaps may start processing smaller cells, if present (e.g., in a diverse population). Thus, using gap size varying along the channel can improve convective intracellular delivery to heterogeneous cell populations. Furthermore, such channels with varying compression gaps can be used to improve cell sorting by reducing the influence of cell size heterogeneity.

Intracellular delivery is controlled by cell compression rate, which is a rate of volume loss by cells in order to pass through the gap formed by a ridge. The cell compression rate can be determined by the flow rate, ridge geometry, a ratio of the gap height to the cell size, ridge width, ridge angle, and compressive surface coating. Furthermore, it has been found that the volume loss (Vloss) increases with the increase in the cell compression rate. Various processing and device characteristics may be specifically selected to achieve the desired cell compression rate. In some examples, ridges 140 are oriented at an angle (a) between 0 degrees to 90 degrees relative to a central flow axis 109 in each channel as, e.g., is schematically shown in FIGS. 2G-2J. More specifically, the ridge angle (a) is between 10 degrees to 30 degrees, or between 30 degrees and 90 degrees, more specifically about 45 degrees. In some examples, ridges 140 form a chevron as, e.g., is shown in FIG. 2G. Alternatively, ridges 140 are straight, e.g., as shown in FIG. 2H. In some examples, ridges 140 are curved as, e.g., is shown in FIGS. 2I and 2J. Furthermore, in some examples, ridges 140 can extend both sidewalls, e.g., as shown in FIG. 2G or, form a sidewall gap with at least one of the sidewall, e.g., as shown in FIG. 2H-2J. This sidewall gap may be referred to as a gutter and may receive uncompressible cells (e.g., pushed along ridges 140 into the sidewall gap) thereby reducing the risk of channel clogging.

It should be noted that the cross-sectional shape of ridges 140 (shown in FIG. 2F) defines the cell compression profile. In some examples, the shape is rectangular (shown in FIG. 2F), or trapezoidal, or triangular. In some examples, ridge surface 142 forming compression gap 141 is substantially flat (e.g., parallel to the second surface 124), or tilted forming a gap varying along the X-axis. In some examples, ridge surface 142 is nearly cylindrical.

Referring to FIG. 2F, spaces within the channel between adjacent ridges 140 and after the last ridge and outlet may be referred to as recovery spaces 145. The length of recovery spaces 145 (in the X direction) between two adjacent ridges may be referred to as ridge spacing (S). The ridge spacing depends on the flow rate, cell characteristics, levels of the previous compression, and such. In some examples, the ridge spacing is between 1 micrometer and 100 micrometers or between 50 micrometers and 10000 microns such as between 200 micrometers and 500 micrometers. The volume of each recovery space 145 and the flow rate determines the average recovery time, i.e., the time that the cells spend in recovery space 145 before being subjected to another compression. It has been found that volume gain (Vgain) is increased when the recovery time is increased. The recovery time can be increased by increasing the length of recovery spaces 145.

Processing Assembly Enclosure Examples

As described above, processing assembly 110 comprises multiple processing components 119 stacked along primary axis 101. Each of processing components 119 comprises multiple channels 139 extending in the direction perpendicular to primary axis 101 and configured for flowing cells. Processing assembly 110 can be enclosed in various enclosure examples, which isolate processing assembly 110 from the environment, provide support to processing assembly 110, and ensure uniform flow of the cell media into each channel 139.

FIG. 3A is a schematic exploded view of an example of cell processing apparatus 100 comprising inlet component 310 (comprising inlet 103) and outlet component 320 (comprising outlet 105), sealed to each other, and enclosing processing assembly 110 comprising multiple processing components 119. FIG. 3B is a schematic cross-sectional view of cell processing apparatus 100 in FIG. 3A. Specifically, inlet component 310 and outlet component 320 define interior cavity 330, which houses processing assembly 110. The shape of interior cavity 330 is specifically defined to ensure that the cell media (generally flowing through cell processing apparatus 100 along the Z-axis) is evenly distributed to each channel 139 of processing assembly 110. It should be noted that multiple channels 139 are positioned on each processing component 119 and offset with respect to each other along the X-axis. Furthermore, multiple processing components 119 are stacked together along the Y-axis, forming processing assembly 110. As such, the shape of interior cavity 330 provides uniform cell media distribution along the X-axis as well as along the Y-axis while the cell media is delivered from inlet 103 to each channel 139, e.g., to ensure the same flow through each channel 139. Similarly, the shape of interior cavity 330 provides the uniform cell media collection along the X-axis as well as along the Y-axis while the cell media exits from each channel 139 and is directed to outlet 105 (e.g., to ensure uniform resistance to the overall flow). It should be noted that the cell media generally flows along the Z-axis. Additional features of interior cavity 330 and channels 139 are shown in FIGS. 3C-3F, illustrating inlet component 310. It should be noted that inlet component 310 and outlet component 320 can have a symmetrical design as, e.g., is shown in FIG. 3B.

FIG. 3C is a schematic top view of inlet component 310 of cell processing apparatus 100 in FIG. 3A. Inlet component 310 is shown to support processing assembly 110. For example, processing assembly 110 can be inserted into inlet component 310 (or outlet component 320) during the assembly of cell processing apparatus 100 before attaching and sealing inlet component 310 and outlet component 320 relative to each other. FIG. 3D is an expanded top view of a portion of inlet component 310 in FIG. 3C, illustrating channels 139 and ridges 140 in processing component 119. While only the top processing component 119 is visible in FIGS. 3C and 3D, any number of processing components 119 can be stacked along the Y-axis. FIGS. 3E and 3F are schematic cross-sectional views of inlet component 310 in FIG. 3C, illustrating a portion of interior cavity 330 and processing components 119 positioned within interior cavity 330, in accordance with some examples.

Figure 4A:
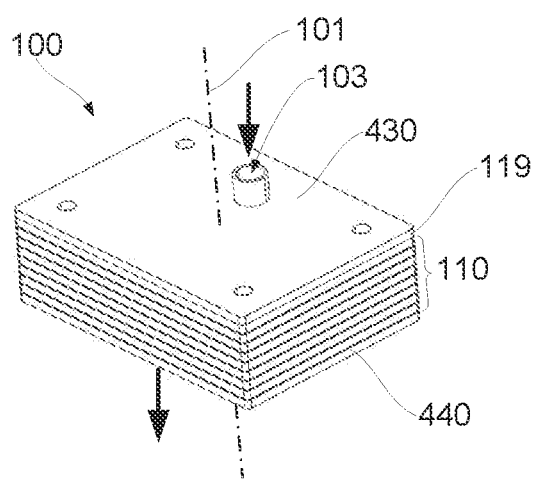
FIG. 4A is a schematic perspective view of yet another example of the cell processing apparatus formed by processing components stacked between an inlet plate and an outlet plate.
Figure 4B:
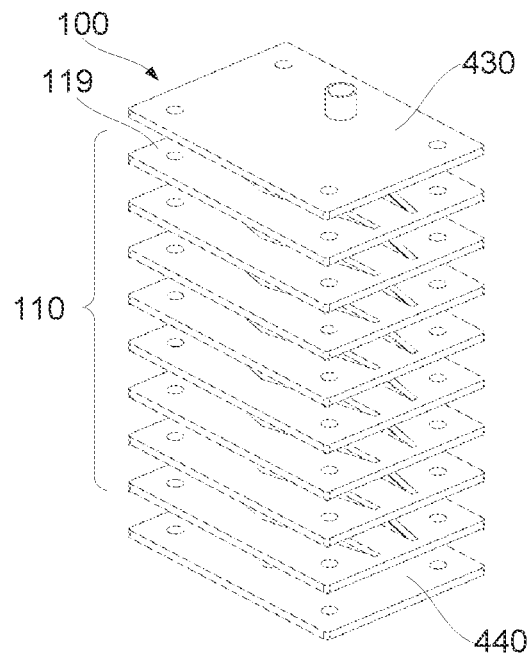
FIG. 4B is a schematic exploded view of the cell processing apparatus in FIG. 4A.
Figure 4C:
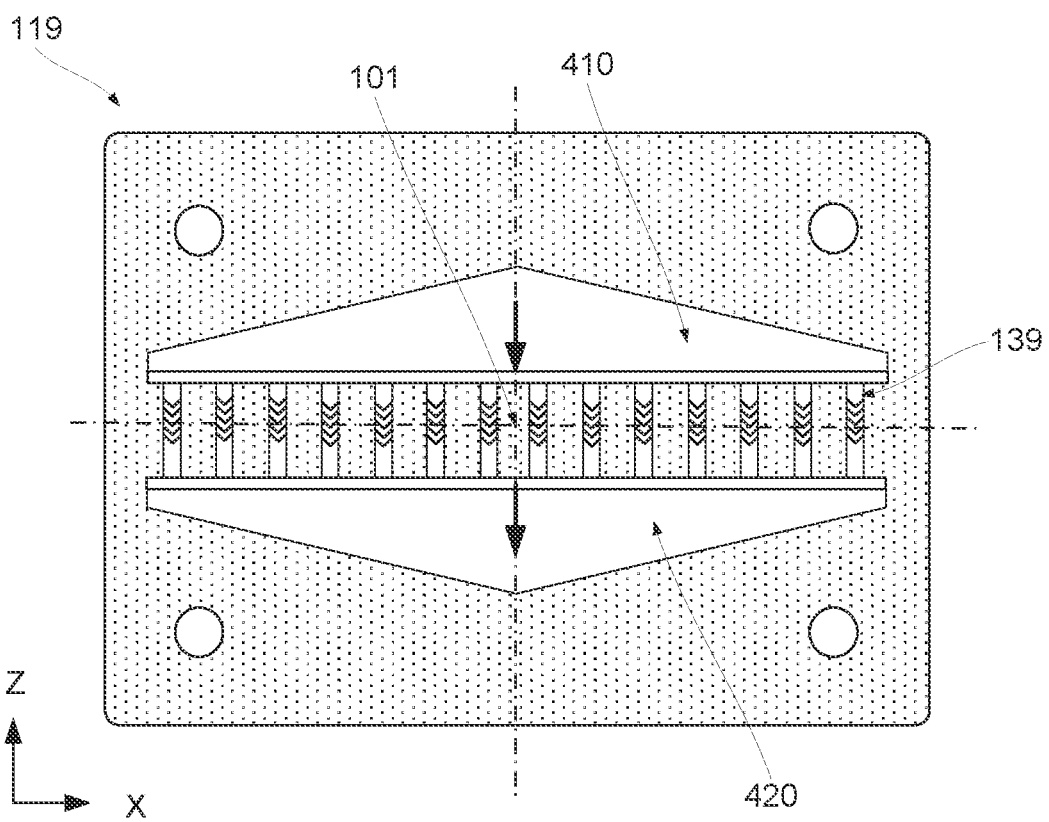
FIG. 4C is a top schematic view of the processing component, used in the cell processing apparatus in FIG. 4A, illustrating inlets and outlets openings and multiple channels extending between these openings.

FIG. 4A is a schematic perspective view of yet another example of cell processing apparatus 100 formed by processing components 119 stacked between inlet plate 430 and outlet plate 440. FIG. 4B is a schematic exploded view of cell processing apparatus 100 in FIG. 4A. In this example, processing assembly 110 is formed by eight processing components 119. However, any number of processing components 119 is within the scope. FIG. 4C is a top schematic view of processing component 119, used in the cell processing apparatus in FIG. 4A, illustrating inlet opening 410 and outlet opening 420. FIG. 4C also illustrates multiple channels 139 extending between inlet opening 410 and outlet opening 420. In this example, each inlet opening 410 and outlet opening 420 has a triangular boundary within a plane perpendicular to primary axis 101 (and parallel to the X-Z plane in FIG. 4C). In some examples, a triangular boundary shape prevents the formation of stagnant zones in the flow.

During the operation of cell processing apparatus 100, the cell media enters cell processing apparatus 100 through inlet plate 430 and is directed to inlet opening 410 of processing component 119, adjacent to inlet plate 430. It should be noted that inlet openings 410 of all processing components 119 can coincide and form a continuous tunnel through cell processing apparatus 100 between inlet plate 430 and outlet plate 440. Similarly, outlet openings 420 of all processing components 119 can coincide and form a continuous tunnel through cell processing apparatus 100 between inlet plate 430 and outlet plate 440. In some examples, the cross-section of inlet opening 410 is the same, and a mirror image of the cross-section of outlet opening 420 as, e.g., is shown in FIG. 4C.

Returning to the operation examples, once the cell media is within inlet opening 410 of processing component 119, adjacent to inlet plate 430, a portion of the cell media flows through channels 139 of this processing component 119 into outlet opening 420. The remaining cell media is directed to inlet openings 410 of other processing components 119. Eventually, all cell media goes through channels 139 of processing components 119 and into the tunnel formed by outlet openings 420 of processing components 119 and then removed from cell processing apparatus 100.

In some examples, cell processing apparatus 100 is assembled by stacking several substantially identical cell processing components 119. While the tunnels, formed by inlet openings 410 and outlet openings 420 of processing components 119, provide uniform distribution and collection of the cell media, these tunnels also require a significant volume of the cell media to fill the tunnels. At least some (or all) of this cell media cannot be recovered from the tunnels. As such, the tunnels represent "dead volume" within cell processing apparatus 100. This "dead volume" can be reduced by special protrusions extending into these tunnels. Specifically, when these external protrusions (e.g., provided as a part of inlet plate 430 and outlet plate 440) allow processing components 119 to be the same and be replaced when needed (e.g., when channels 139 of processing components 119 become blocked). These protrusions features will now be described with reference to FIGS. 4D-4G.

Specifically, FIG. 4D is a schematic perspective view cell processing apparatus 100 with processing components 119 stacked between inlet plate 430 and outlet plate 440. FIG. 4E is a schematic cross-sectional view of cell processing apparatus 100 in FIG. 4D. FIG. 4F is an exploded cross-sectional view of cell processing apparatus 100 in FIG. 4D, providing additional representation of some components and features. Inlet plate 430 comprises inlet protrusion 432 extending into outlet opening 420 of each of processing components 119 and occupying a different volume in outlet openings of different ones processing components 119. Specifically, inlet protrusion 432 is tapered and blocks the most volume in outlet opening 420 of the closest (adjacent) processing component 119 and the least volume in outlet opening 420 of the furthest processing component 119. As such, the unblocked volume is the largest in the closest (adjacent) processing component 119 since outlet opening 420 carries the least amount of cell media (out of all processing components 119), i.e., the only the cell media that have flown through this closest (adjacent) processing component 119. Outlet opening 420 of the next processing component 119 carries the cell media that have flown through this next processing component 119 also received from the closest (adjacent) processing component 119. Finally, outlet opening 420 of the furthest processing component 119 carries all cell media going through all processing components 119, thereby needing the most unblocked volume. In a similar manner and with reference to FIG. 4G, outlet plate 440 comprises outlet protrusion 442 extending into inlet opening 410 of each of processing components 119 and occupying a different volume in outlet opening 420 of a different one processing components 119. The same principle of different volumetric flow rates through each inlet opening 410 applies on the inlet side. This matching of different volumetric flowrates (at different positioned within the inlet and outlet tunnels) and different cross-sectional areas of these tunnels (provided by different blocked volumes by inlet protrusion 432 and outlet protrusion 442) produce more uniform linear flow rates within cell processing apparatus 100 as will now be described with reference to FIG. 4H Cell media is supplied into each one of channels 139 using various distribution pathways. These pathways are specifically designed such that the linear flow rate through each channel 139 is substantially the same. This flowrate uniformity ensures that all cells are processed in a similar manner, e.g., subjected to the same compression rate, for the same period, and allowed the same relaxation time. These pathways are provided by various components of cell processing apparatus 100 such as distribution component 106, processing assembly 110, and/or other components.

Figure 4H:
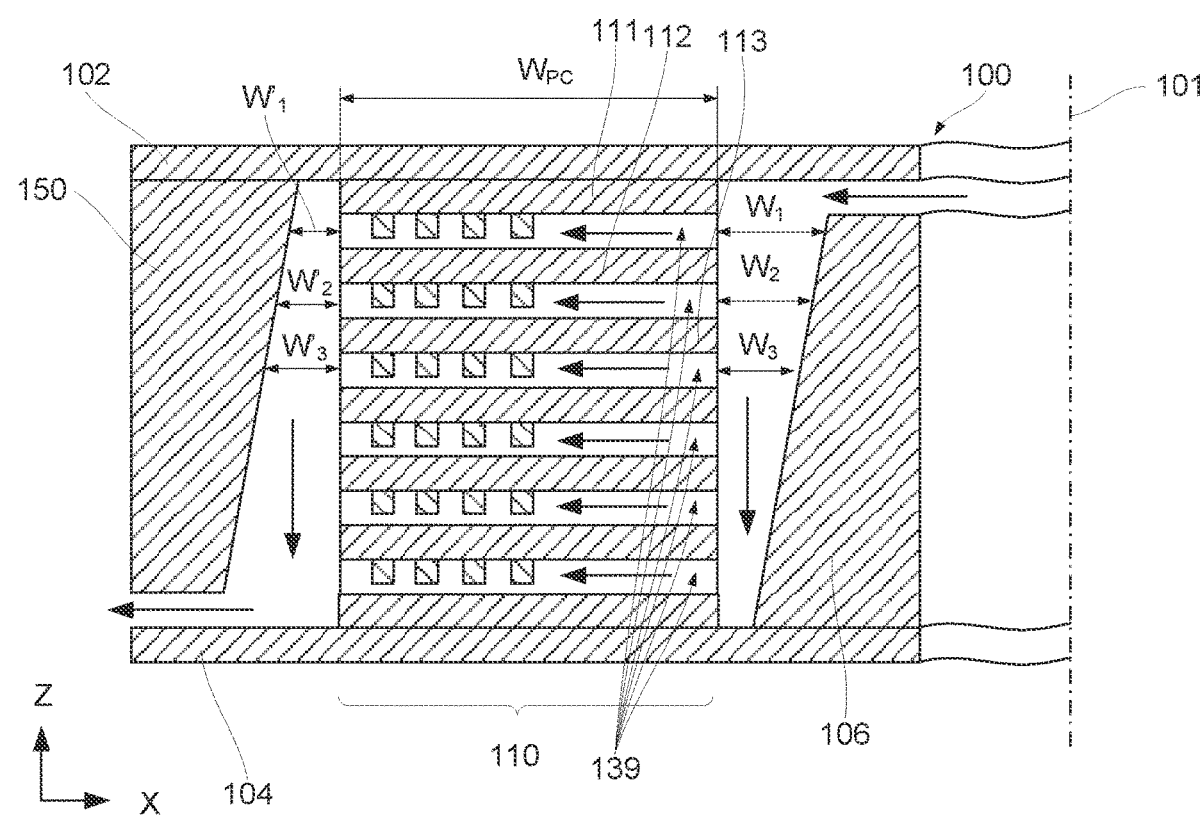
FIG. 4H is a schematic cross-sectional view of another example of the cell processing apparatus.

FIG. 4H illustrates a cross-sectional side of a portion of cell processing apparatus 100, in accordance with some examples. Specifically, FIG. 4H illustrates distribution component 106, outer wall 150, and processing assembly 110, positioned between distribution component 106 and outer wall 150. The space between distribution component 106 and processing assembly 110 is used to supply the cell media to channels 139 within processing assembly 110. The space between outer wall 150 and processing assembly 110 is used to remove the cell media that passed through channels 139. FIG. 4H also illustrates the cell media is being delivered to the space between distribution component 106 and processing assembly 110 at the top of cell processing apparatus 100, adjacent to inlet component 102. The cell media is being removed from the space between outer wall 150 and processing assembly 110 at the bottom of cell processing apparatus 100, adjacent to stopper 104.

The cross-section in FIG. 4H illustrates six channels 139 stacked vertically between inlet component 102 and stopper 104. As the cell media enters the space between distribution component 106 and processing assembly 110 the cell media is directed into channels 139. For clarity, a channel formed by processing component 111 and second processing component 112 may be referred to as a first channel, while a channel formed between second processing component 112 and third processing component 113 may be referred to as a second channel. As the cell media enters the first channel, the volumetric flow rate of cell media traveling into space between distribution component 106 and processing assembly 110 past the first channel is less. Additional reduction on the volumetric flow rate appears after each new channel as each channel allows some of the cell media to flow through the channel. If the cross-section of the space between distribution component 106 and processing assembly 110 remains constant, then the linear flow rate of the cell media will drop proportionally to the volumetric flow rate. The width reduction ($W_1 > W_2 > W_3$) shown in FIG. 4H allows maintaining the linear flow rate of the cell media substantially constant within the space between distribution component 106 and processing assembly 110. Similar but the inverse process occurs in the space between outer wall 150 and processing assembly 110. The volumetric flow rate in that space increases from top to bottom as additional cell media is received from each new channel. As such, the width of this space is increased from top to bottom ($W'_1 < W'_2 < W'_3$). Overall, the cross-sectional area of supply channels varies between channel layers such that the linear flow velocity is uniform throughout all parts of cell processing apparatus 100. This can prevent the formation of stagnation zones in the flow.

Figure 5A:
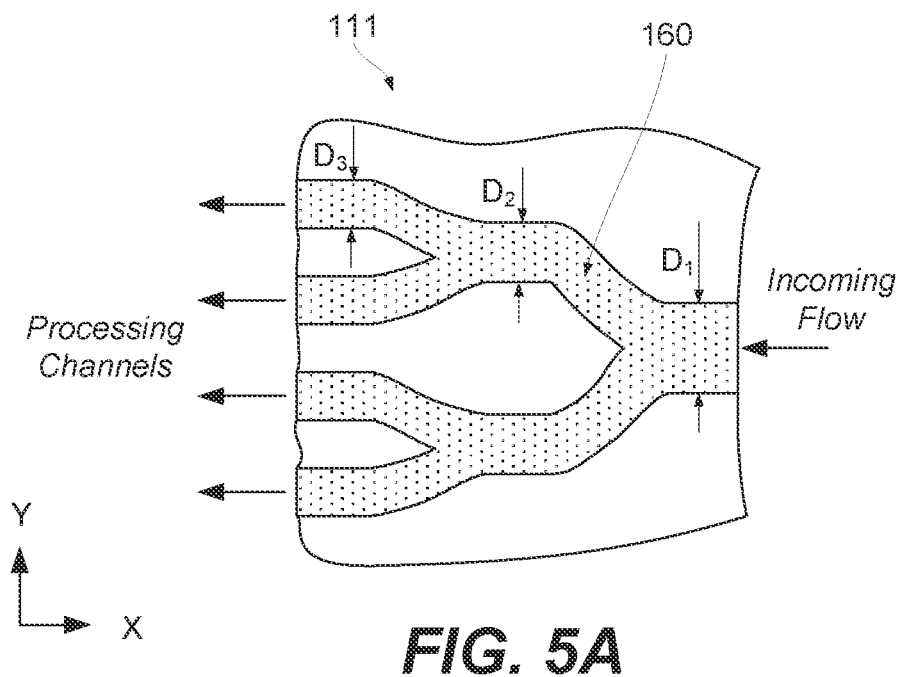
FIG. 5A is a schematic top cross-sectional view of delivery channels extending through the processing component, in accordance with some examples.

In some examples, one or more of the processing components comprise distribution and/or collecting pathways. These pathways should be distinguished from processing channels, which comprise compressive ridges. FIG. 5A illustrates an example of distribution pathway 160, arranged into a tree-like structure. Each distribution pathway channels branches to two identical sub-pathways, at each branching level, to provide equal flow conditions for each branch (e.g., using specific diameters in each branch of these pathways). These sub-pathways may be also referred to as branching pathways. This branching structure ensures that each channel 139 has the same linear flow rate. Furthermore, when the cross-section of all channels 139 is the same, the volumetric flow rate is also the same. While FIG. 5A illustrates a two-way split, one having ordinary skill in the art would understand that a split includes any number of sub-pathways (two, three, four, and so on). Furthermore, while FIG. 5A illustrates two levels of splits, one having ordinary skill in the art would understand that a split includes any number of these split levels (two, three, four, and so on).

Overall, the configuration is shown in FIG. 5A and other like configurations can be used to ensure that all processing channels are supplied by identical amounts of media, reagents, and cells which are required for maintaining product quality and consistency. To maintain similar flow velocity in the distribution and collection channels, the total channel cross-section area (i.e. the sum of channel cross-section areas at each level of branching) can be kept constant at each branching level (distributing and collecting), such that $A_{total} = N*A$, where $A = H*W$ and N it the number of channels. The channel dimensions can be set such that W/H did not exceed 20 due to fabrication constraints, such as wall sagging when channels are excessively wide. The number of parallel microchannels can be limited by the fabrication process, the footprint of the microchannel layout with distributing and collecting channel networks, air bubble formation in microchannels preventing or altering the fluid flow, and the cross-sectional dimensions of the supply channels. Similarly branching channel structures can be used at the outlet to collect the media and processed cells. Such arrangement of the outlet section can be used to ensure similar flow resistance over each processing channel 139.

Figure 5B:
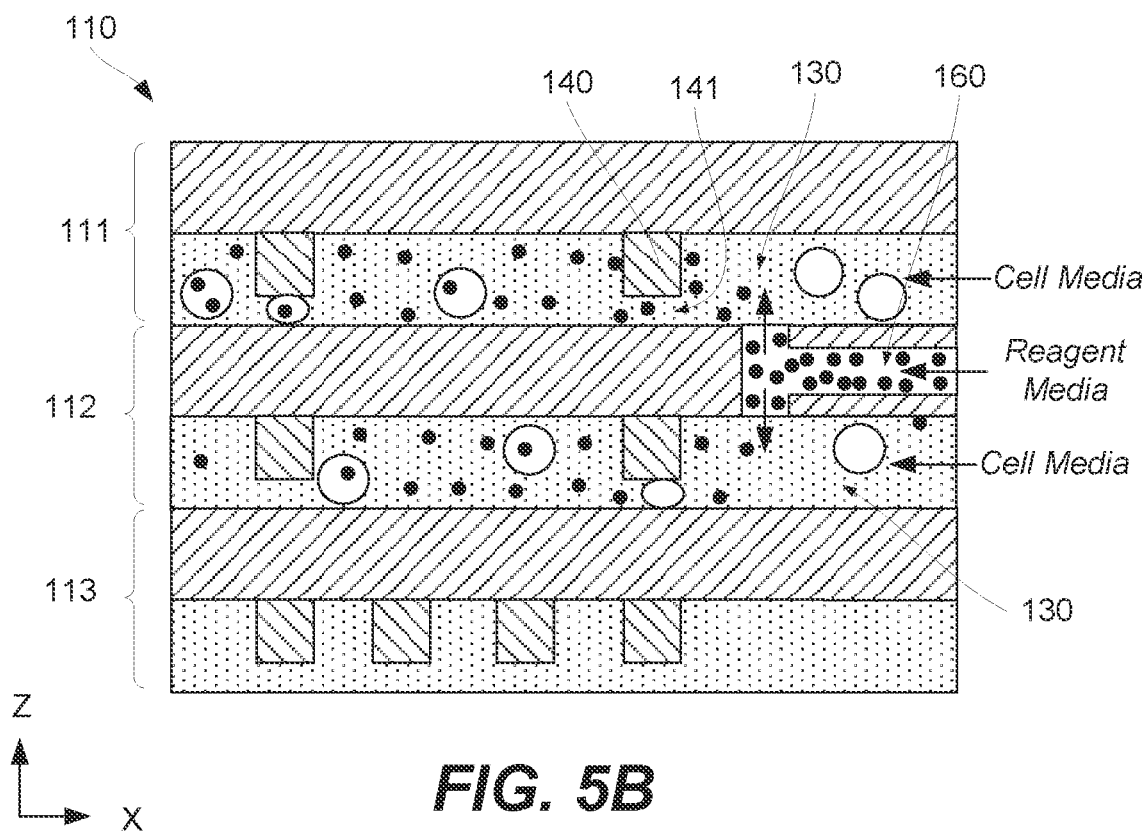
FIG. 5B is a schematic side cross-sectional view of delivery channels in two processing components, in accordance with some examples.
Figure 5C:
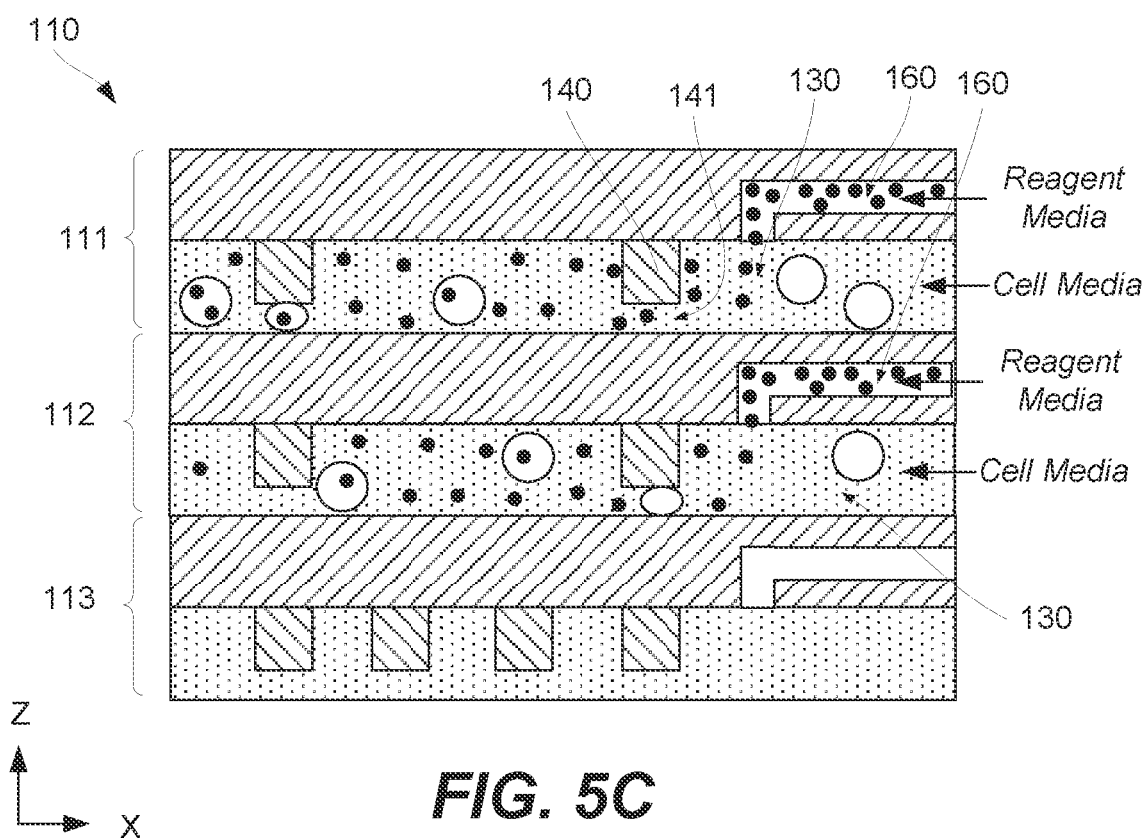
FIG. 5C is another example of processing components, showing delivery channels in these components.

FIG. 5B illustrates another example of distribution pathway 160 provided in processing components or, more specifically, in second processing component 112, stacked between processing component 111 and third processing component 113. In this example, distribution pathway 160 is in fluidic communication with two channels, channel 130 formed by processing component 111 and second processing component 112, and also channel 130 formed by second processing component 112 and third processing component 113. As such, distribution pathway 160 can be provided in every other processing component. FIG. 5C illustrates another component where distribution pathway 160 is provided in each processing component.

Distribution pathway 160 is shown in FIGS. 5B and 5C can be used for more efficient use of reagents (e.g., reduce the volume of expensive reagents needed). In these examples, reagents can be supplied directly into the processing channels 130 using distribution pathway 160 without premixing with media-containing cells, at least outside premixing of processing assembly 110. This approach can be used also when reagents are unstable and degrade in cell media. In some examples, the flow rate of reagents is lower than the flow rate of cell media by at least about 10, 100, or even 1000 times. In these examples, distribution pathways 160 can have much smaller cross-sectional areas in comparison to processing channels 130. Furthermore, the pressure in distribution pathways 160 is matched or exceeds the pressure in processing channels 130 to prevent the backflow of cell media into distribution pathways 160.

Arrangements of processing channels 130 in processing components 119 may depend on the shape of processing components 119 and overall processing assembly 110. For example, FIG. 2A illustrates round processing components 119. In this example, processing channels 130 extend radially, e.g., from primary axis 101 of cell processing apparatus 100. When processing components are rectangular, processing channels 130 may extend parallel to each other. The use of circular layers has the advantage of a simpler stack design where leaks can be prevented using ring-shaped rubber gaskets placed between individual layers. In contrast, using rectangular-shaped layers can require the use of gaskets to prevent fluid leads at the corners to the assembly that are more prone to leaking.

In some examples, processing components 119, which comprise ridges 140 are alternated with reagent delivery components, which do not have ridges. In these examples, processing channels 130 may be formed entirely by processing components 119 or by stacking processing components 119 with reagent delivery components.

Channel design can include structural elements enhancing the mixing of the reagents with media such as pillars, ridges, channel constrictions. Actuated mixing elements can be included such as magnetic beads, magnetic filaments, and acoustically driven filaments. The mixing ensures uniformity of the media.

In some examples, the apparatus can include a plurality of cell processing apparatuses 100 arranged in parallel. The use of multiple parallel devices simultaneously can be limited by the requirement for the overall flow rate in the apparatus. In some examples, the flow is supplied sequentially to different devices. The flow is directed to the next device when significant clogging is detected reducing the flow rate. In some examples, the flow switching from one device to another is controlled by monitoring the flow rate within the supply channel. In some examples, a plurality of cell processing apparatuses 100 are connected in series to provide multistep mechanoporation. In some examples, the serial connection of multiple cell processing apparatuses 100 is implemented to improve delivery efficiency or to deliver different payloads sequentially into the cell population.

Filter and Separation Integration Examples

In some examples, cell processing apparatus 100 is configured to perform additional functions, besides mechanoporation. Furthermore, one of these additional functions may be performed in the same processing assembly where mechanoporation is performed. For example, processing components may be configured to perform filtering and cell separation.

Figure 6A:
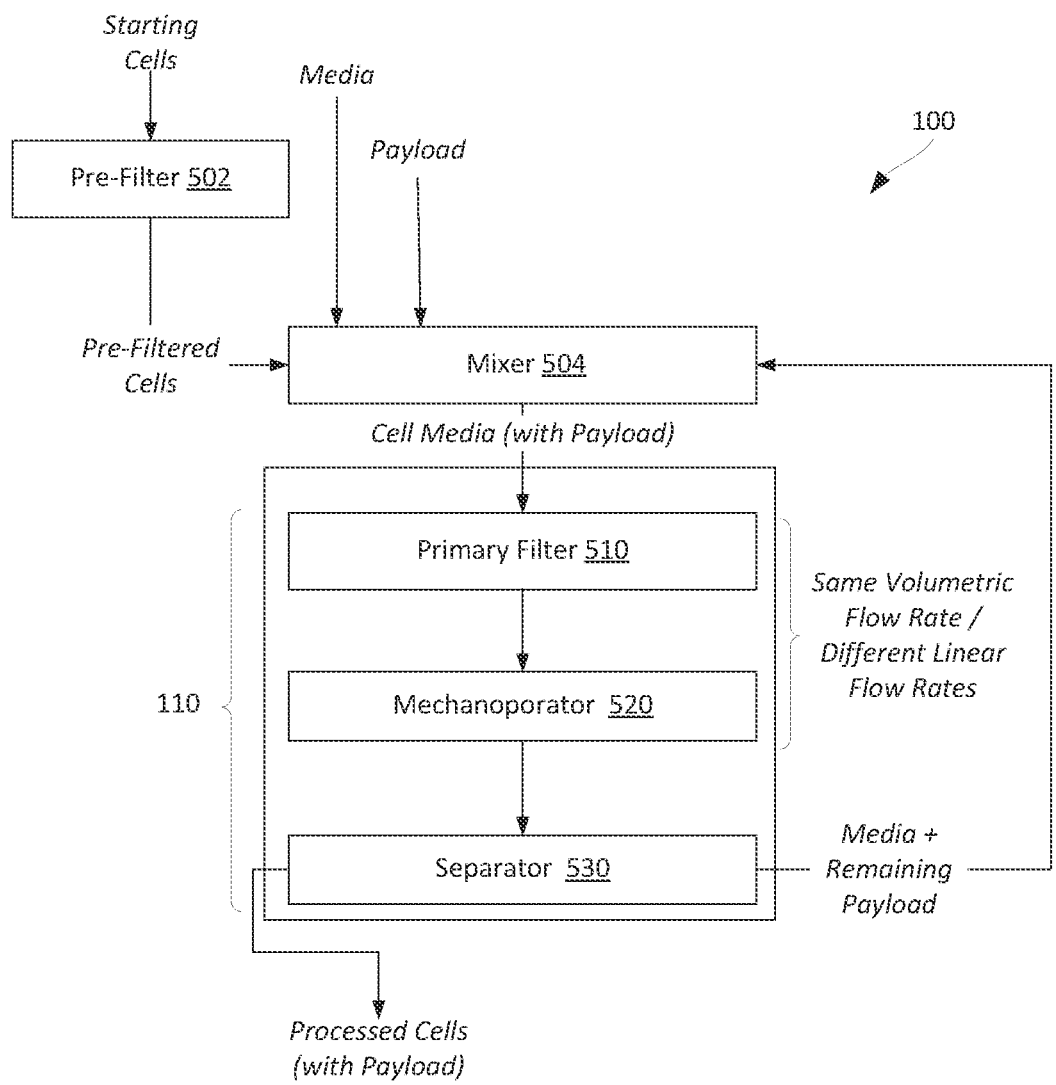
FIG. 6A is a block diagram of a processing system, showing the integration of various components in a processing assembly, in accordance with some examples.

FIG. 6A is a schematic illustration of cell processing apparatus 100 comprising processing assembly 110, which in turn comprises primary filter 510, mechanoporation 520, and separator 530. Each of primary filter 510, mechanoporator 520, and separator 530 is formed by one or more processing components. However, the configurations of these processing components is different for each of primary filter 510, mechanoporator 520, and separator 530 as further described below with reference to FIGS. 6B and 6C. FIG. 6A also illustrates pre-filter 502 and mixer 504 as additional components of cell processing apparatus 100. These components may be separate from processing assembly 110.

Cells are initially delivered into pre-filter 502. The purpose of the pre-filter is to remove (from the media) any synthetic and biological particles that are significantly greater than the average cell size and can lead to clogging of the processing microchannels. Some examples of the pre-filters include, but are not limited to, arrays of posts with separation comparable to the average cell size, and cross-channel ridges forming a gap that is similar to the gap in the processing channel.

Pre-filtered cells are then delivered from pre-filter 502 into mixer 504. In some examples, media (e.g., a liquid base) and/or payload are also delivered into mixer 504. Mixer 504 combined the cells with the media and payload, forming a cell media. The cell media is then delivered into processing assembly 110. More specifically, the cell media is first delivered into primary filter 510 where cells are filtered based on their compressibility. In some examples, cells are mixed with payload using a mixer 504 after primary filter 510. The cells, which passed primary filter 510, are then delivered to mechanoporator 520. Mechanoporator's functions are described above. Processed cells are then flown from mechanoporator 520 to separator 530. Each of these components will now be described in more detail.

Similar to mechanoporator 520, primary filter 510 is formed from processing components, which are stacked together along primary axis 101 of cell processing apparatus 100. The processing components of primary filter 510 may be stacked together with the processing components of mechanoporator 520. However, the processing components of primary filter 510 are different from the processing components of mechanoporator 520 as further described below with reference to FIGS. 6B and 6C. Primary filter 510 is configured to capture abnormal cells and other particles that due to their size or mechanical properties cannot pass through the gaps of mechanoporator 520 and can be stuck in the processing channels of mechanoporator 520, leading to clogging of mechanoporator 520.

Figure 6B:
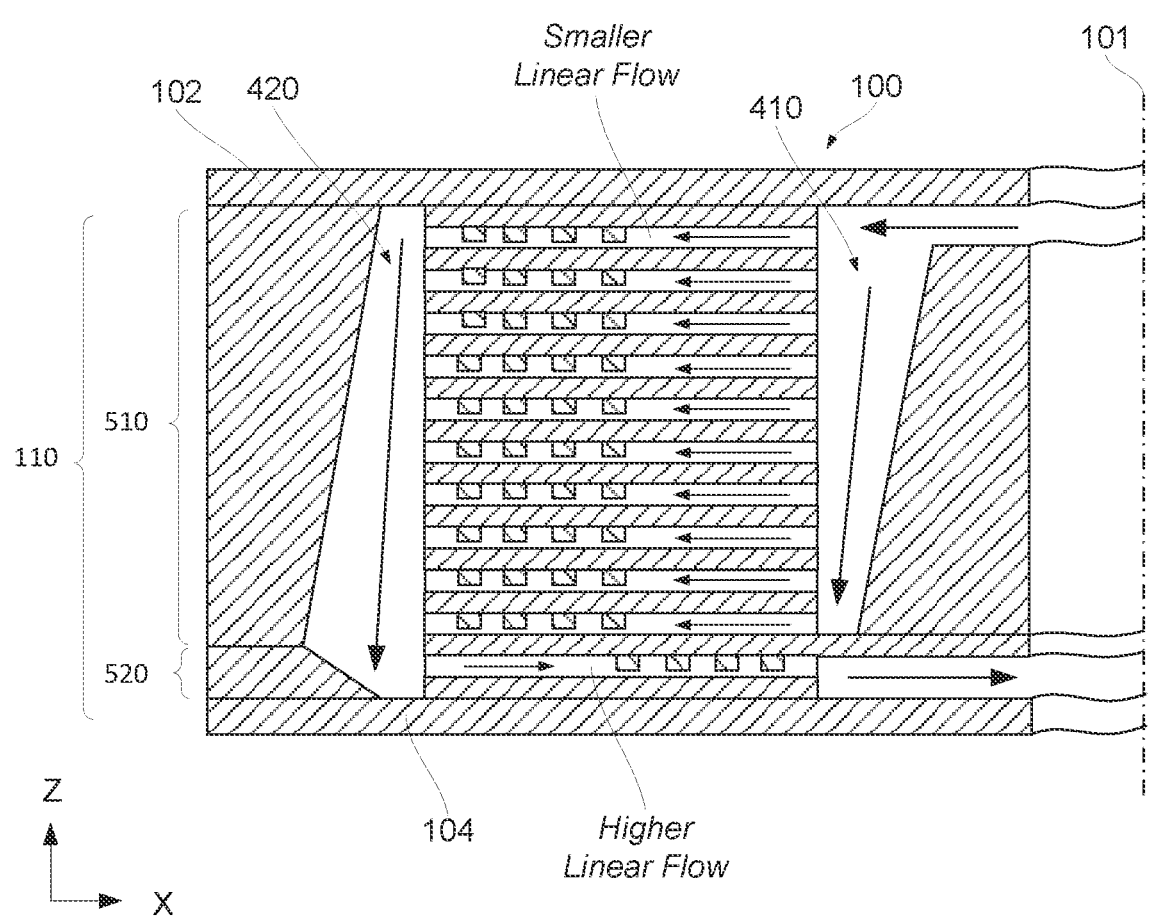
FIG. 6B is a schematic side cross-sectional view of a processing assembly, showing the integration of various components in the processing assembly, in accordance with some examples.

In some examples, the linear flow velocity of the cell media through primary filter 510 is less than the linear flow velocity through mechanoporator 520 (e.g., at least about 2 times less, at least about 5 times less, or even about 10 times less). The lower flow velocity through primary filter 510 is used to prevent damage of cells as cells pass near captured particles and uncompressible cells in primary filter 510. In some examples, the difference in the linear flow velocity is achieved by using a larger number of processing components (and corresponding channels) in primary filter 510 than in mechanoporator 520 as, e.g., is schematically shown in FIG. 6B. FIG. 6B illustrates cell processing apparatus 100 comprising processing assembly 110 formed by primary filter 510 and mechanoporator 520. The number of processing components in primary filter 510 is greater than in mechanoporator 520, e.g., at least about 2 times greater, at least about 5 times greater, or even about 10 times greater. Assuming that each processing component in primary filter 510 and mechanoporator 520 has the same number of channels and these channels have the same average cross-section, then the ratio of the linear flowrate through each channel in primary filter 510 and the linear flowrate through each channel in mechanoporator 520 is inverse-proportional to the ration of the number of processing components in primary filter 510 to the number of processing components in mechanoporator 520. As such, the number of processing components in primary filter 510, mechanoporator 520, and other sub-assemblies of processing assembly 110 can be used to control linear flow rates through each of these sub-assemblies. It should be noted that the volumetric flow rate through each of these sub-assemblies is the same. Overall, primary filter 510, mechanoporator 520, and other sub-assemblies can be integrated into the same processing assembly 110. Alternatively, these sub-assemblies can be standalone components.

Referring to FIG. 6A, after passing through mechanoporator 520, the cell media can be supplied to separator 530 that separates processed cells and from the rest of the cell media (e.g., media and remaining payload). These media and remaining payload can be recycled (e.g., supplied back to mixer 504) where these components are combined with new cells, additional payload, and/or additional media (e.g., to achieve the desired composition of the cell media supplied into processing assembly). The amount of new reagent can be defined based on the separation efficiency of separator 530.

Figure 6C:
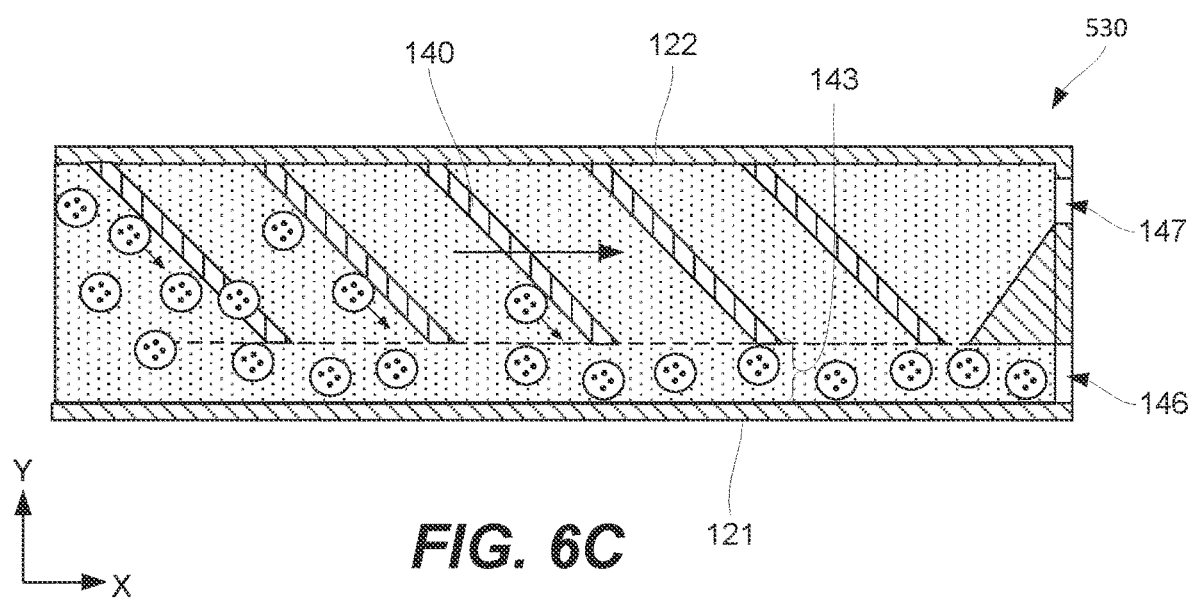
FIG. 6C is a schematic top cross-sectional view of a channel in a separator, in accordance with some examples.

Referring to FIG. 6C, in some examples, separator 530 comprises diagonal ridges 140 that concentrate cells along one side of the channel, e.g., first divider wall 121. The spacing between the ends of ridges 140 and first divider wall 121 may be referred to as sidewall gap 143 (or "gutter"). As the cells flow through the channel and encounter ridges 140, ridges 140 direct the cells toward sidewall gap 143 while allowing the rest of the media (including the remaining payload) to flow through the separation gap between ridges 140 and another wall of the channel. The separation gap is similar to gap 141 described above with reference to FIG. 2F and used to compress cells. Separator 530 also comprises first outlet 146, aligned with sidewall gap 143, and used to remove processes cells from separator 530. Furthermore, separator 530 comprises second outlet 147 for removing the rest of the media (separated from the processed cells). As noted above, this media can be returned back to mixer 504.

In some examples, cell processing apparatus 100 comprises sensors for process control, such as pressure, temperature, and oxygen sensors. For example, pressure sensors are positioned in an inlet (before the processing channel) and in an outlet (after processing channels) to determine the pressure drop across the processing channels or, more specifically, across primary filter 510 and/or across mechanoporator 520. The monitoring pressure differential can be used to determine clogging. In some examples, chemical sensors are used to control cell conditions. Flow sensors can be used to control flow rates. The signals from the sensors can be used to control the operations of various devices (e.g., pumps, cell media supply, and the like). For example, pressure and flow data can be used to control the functionality of the filtration element. When the filtration element traps a significant amount of particles and abnormal cells, the reduced flow rate or increased pressure can be used to interrupt the processing and replace or flush the filtration element.

Figure 7A:
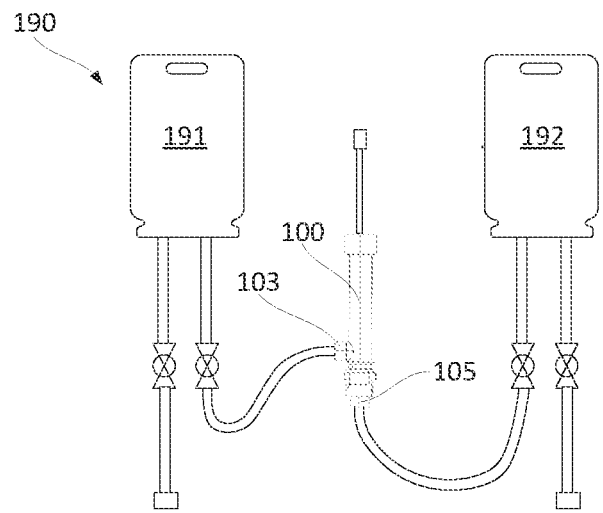
FIG. 7A is a schematic representation of another example of the processing system comprising a cell processing apparatus.

FIG. 7A is a schematic representation of another example of processing system 190 comprising cell processing apparatus 100. Cell processing apparatus 100 comprises inlet 103 and outlet 105. Inlet 103 is used for connection to cell media source 191, such as a sterile bag. Outlet 105 is used for connection to cell media receiver 192, such as a sterile bag. While not specifically identified in FIG. 7A, processing system 190 can also include various valves, connectors, and the like.

Figure 7B:
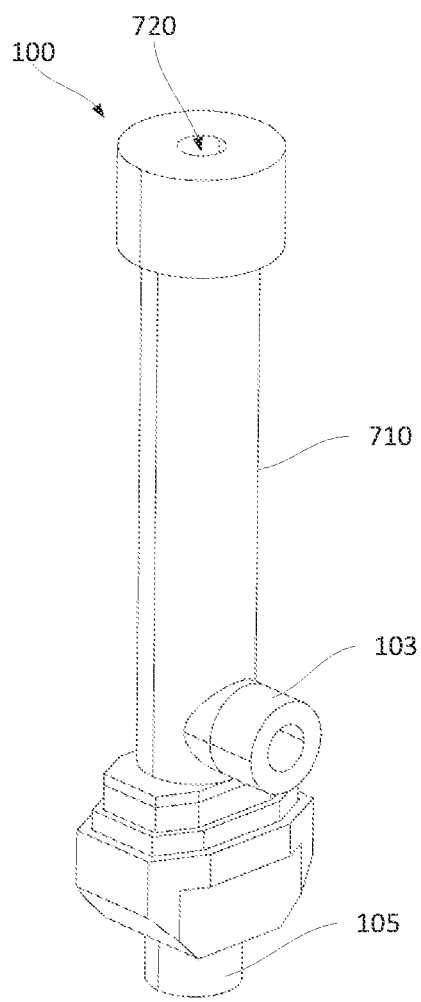
FIG. 7B is a schematic perspective view of the cell processing apparatus in FIG. 7A.
Figure 7C:
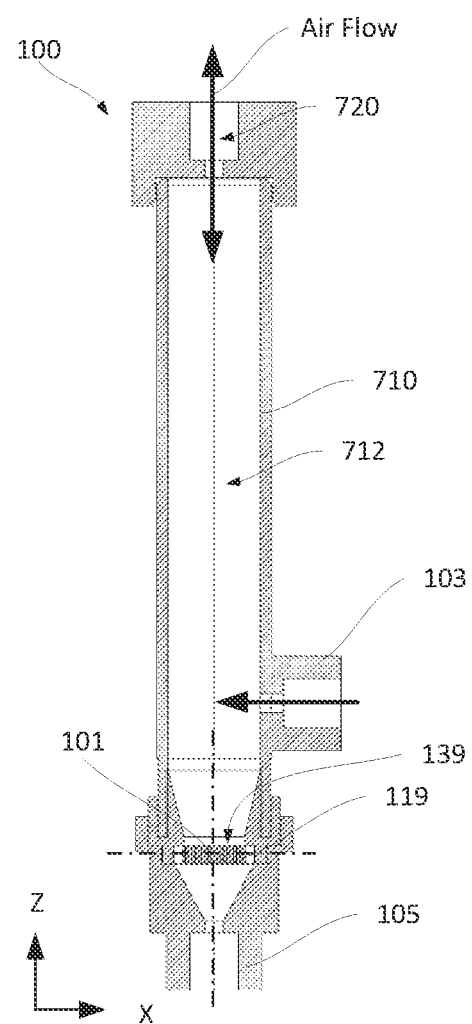
FIG. 7C is a schematic cross-sectional view of the cell processing apparatus in FIG. 7B.

Referring to FIGS. 7B and 7C, cell processing apparatus 100 comprises cell media collector 710 comprising collector cavity 712 and collector port 720. During the operation of processing system 190, collector cavity 712 is first filled with the cell media (e.g., from cell media source 191). For example, a reduced pressure (e.g., between 1 Pa and 1 kPa) can be created in collector cavity 712, using a device (e.g., a vacuum pump) fluidically coupled to collector port 720. This reduced pressure causes the cell media to fill collector port 720. It should be noted that during this cavity-filling operation, the flow through outlet 105 is blocked (e.g., using an outlet valve). Once collector cavity 712 is filled, the flow through inlet 103 is blocked (e.g., using an inlet valve), while the flow-through outlet 105 is enabled. Collector cavity 712 can be pressurized (e.g., between $10^5$ Pa and $10^6$), using the same or a different device fluidically coupled to collector port 720. This pressure causes the cell media to flow through processing components 119 or, more specifically, through channels 139 in processing components 119.

Referring to FIG. 7C, outlet 105 is fluidically coupled to each of the multiple channels 139. Collector cavity 712 is fluidically coupled with the collector port 720, inlet 103, and each of multiple channels 139. Collector port 720 can be used for connection to a gas flow source. In this example, inlet 103 is positioned closer to processing assembly 110 than to collector port 720. This approach exerts less mechanical stress on the cell media (gentler filling) compared to the top filling. Furthermore, bottom filling generates less foaming. In some examples, a top-filled device is equipped with a liquid guide feature to prevent the cell media (liquid) from falling down/splashing in a collector cavity.

Figure 7D:
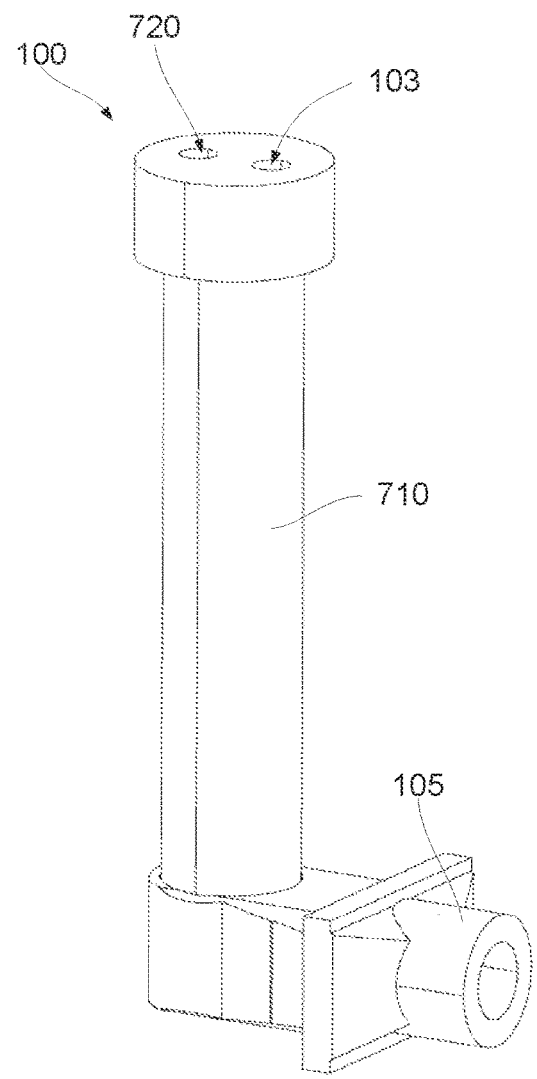
FIGS. 7D and 7E illustrate a schematic perspective view and a cross-sectional view of another example of the cell processing apparatus.
Figure 7E:
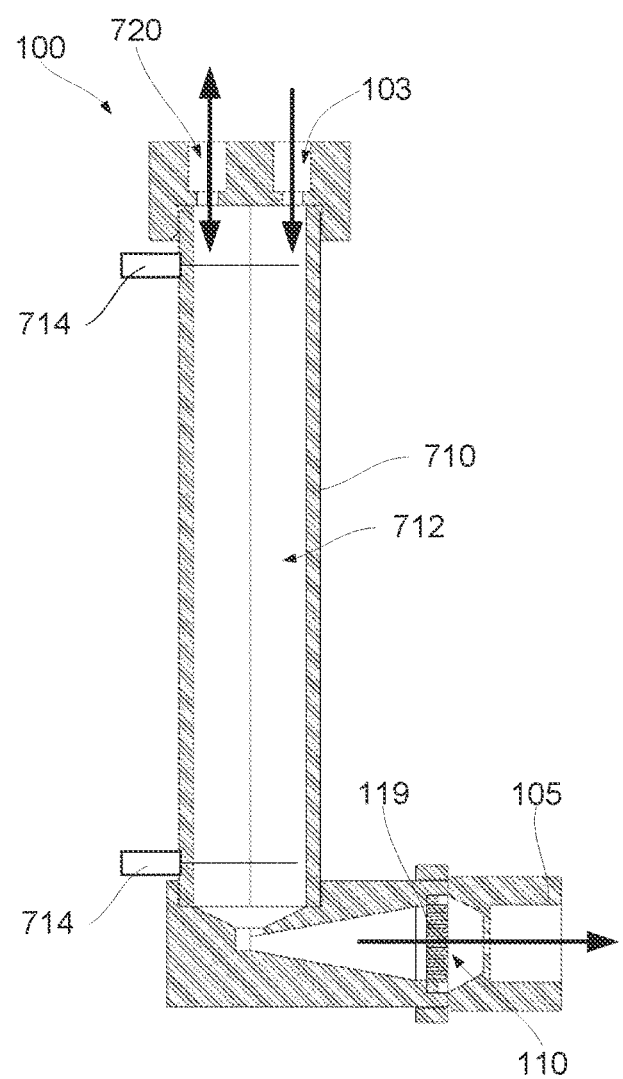
Figure 8A:
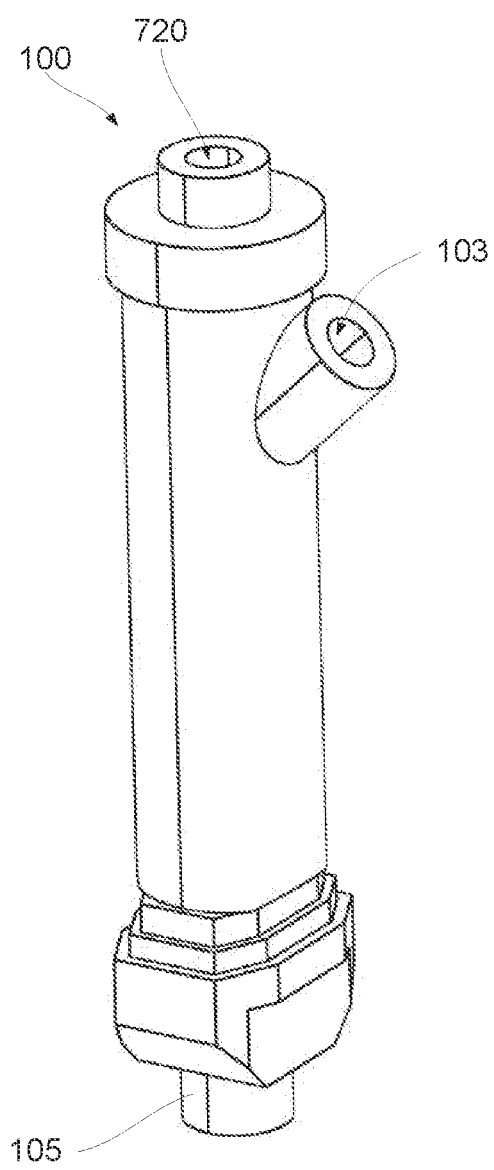
FIGS. 8A and 8B are schematic perspective views of two additional examples of the cell processing apparatus.
Figure 8B:
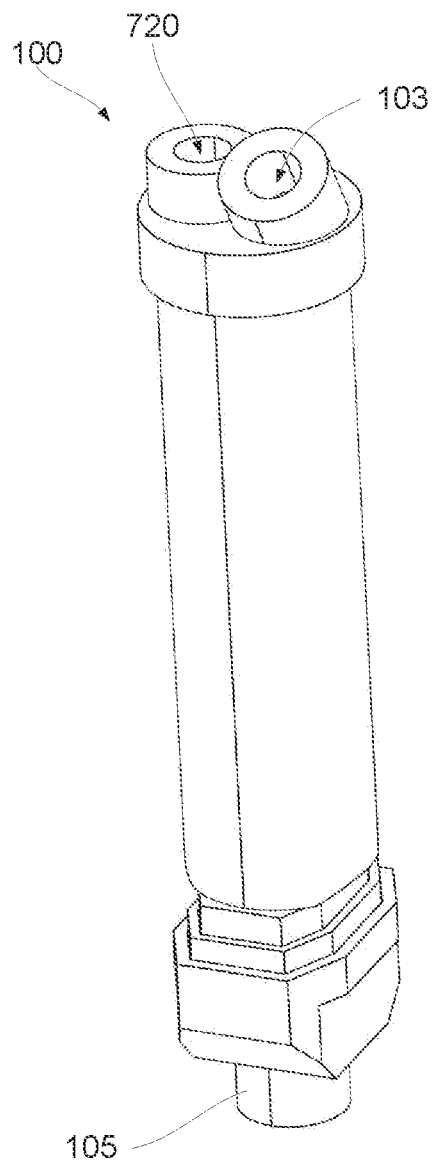

FIGS. 7D and 7E as well as FIGS. 8A and 8B are schematic views of additional examples of cell processing apparatus 100, in which inlet 103 is positioned closer to collector port 720 than to processing assembly 110. It should be noted that during filling, some air bubbles can be introduced to cell processing apparatus 100. The top filling approach minimizes bubble formation by releasing air from the top. If the liquid is filled from the bottom and there is some air inside the liquid initially, the air has to pass through the liquid to escape, which may cause bubbles and confuse the liquid level sensors. The top filling approach helps with preventing bubble formation, e.g., allowing air to escape from the top and avoid bubble trapping.

Referring to FIG. 7E, in some examples, cell media collector 710 further comprises one or more level sensors 714 for measuring one or more levels of cell media within the collector cavity 712. Some examples of level sensors 714 include, but are not limited to, capacitance sensors, ultrasonic sensors, and magnetic sensors. When magnetic sensors are used, a floater with a magnet can be positioned in the cavity. The floater changes the position with the level of the cell media.

Operating Method Examples

Figure 9:
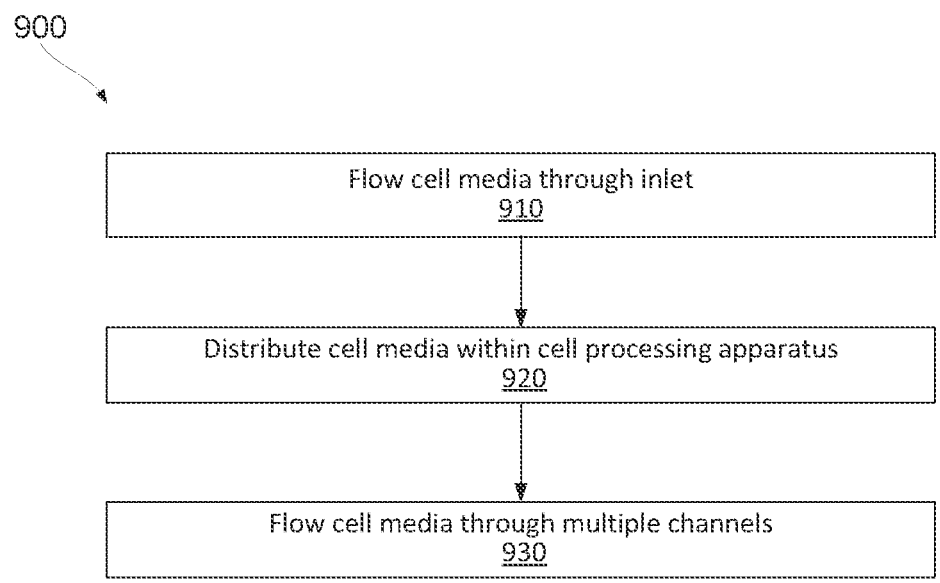
FIG. 9 is a process flowchart corresponding to a mechanoporation method of processing cells using a cell processing apparatus, in accordance with some examples.

FIG. 9 is a process flowchart corresponding to mechanoporation method 900 of processing cells using cell processing apparatus 100, in accordance with some examples. Various examples of cell processing apparatus 100 are described above.

Mechanoporation method 900 comprises (block 910) flowing the cell media comprising cells through inlet 103 of cell processing apparatus 100. In some examples, the cell media is agitated in cell media source 191 to prevent cell gravitational sedimentation. Such agitation can be achieved by a mechanical or magnetic agitator causing temporal or continuous media motion in the cell media source 191.

Mechanoporation method 900 also comprises (block 920) distributing the cell media within cell processing apparatus 100 among multiple channels 139 in each of processing components 119 stacked along primary axis 101 of cell processing apparatus 100.

Mechanoporation method 900 further comprises (block 930) flowing the cell media through multiple channels 139. Each channel 139 comprises one or more ridges 140. Each ridge 140 forms gap 141 with an adjacent one of processing components 119 such that gap 141 is smaller than the diameter of the cells in the cell media. Flowing the cell media through multiple channels 139 causes the compression of cells while cells pass through gap 141 as, e.g., described above with reference to FIG. 2F.

Furthermore, flowing the cell media through multiple channels 139 is performed while a portion of cell media experiences the same pressure upon entry into each of multiple channels 139. This same pressurization feature is achieved by an air pump or another pressure source.

CONCLUSION

Although the foregoing concepts have been described in some detail for purposes of clarity of understanding, it will be apparent that certain changes and modifications may be practiced within the scope of the appended claims. It should be noted that there are many alternative ways of implementing the processes, systems, and apparatuses. Accordingly, the present examples are to be considered illustrative and not restrictive.

The invention claimed is:

1. A cell processing apparatus for processing cells using mechanoporation, the cell processing apparatus comprising:
   an inlet plate comprising an inlet opening;
   an outlet plate comprising an outlet opening; and
   a processing component stacked between the inlet plate and the outlet plate, wherein:
      the processing component comprises dividers, each comprising a first divider wall, a second divider wall, and a first surface, extending between the first divider wall and the second divider wall,
      the processing component further comprises a channel wall, ridges protruding from the channel wall, and a second surface,
      the first surface of the processing component directly contacts one of the inlet plate and the outlet plate,
      the first divider wall, the second divider wall, the channel wall of the processing component and the one of the inlet plate and the outlet plate define multiple channels, each fluidically coupled and extending between the inlet opening and the outlet opening and configured for flowing a combination of a cell media and the cells such that one or more of the ridges of the processing component extend into each of the multiple channels, and
      each of the ridges of the processing component forms a gap with the one of the inlet plate and the outlet plate such that the gap is smaller than a diameter of at least one of the cells thereby causing compression of the at least one of the cells while the cells pass through the gap.

2. The cell processing apparatus of claim 1, wherein the first surface of the processing component directly contacts the inlet plate.

3. The cell processing apparatus of claim 2, further comprising a second processing component, wherein:
   the processing component comprises a second surface opposite the first surface,
      the second processing component further comprises dividers, each comprising a first divider wall, a second divider wall, and a first surface, extending between the first divider wall and the second divider wall of the second processing component,
   the second processing component further comprises a channel wall, ridges protruding from the channel wall, and a second surface,
   the first surface of the second processing component directly contacts the second surface of the processing component,
   the first divider wall, the second divider wall, the channel wall of the second processing component and the second surface of the processing component define multiple channels, each fluidically coupled and extending between the inlet opening and the outlet opening and configured for flowing the combination of the cell media and the cells such that one or more of the ridges of the processing component extend into each of the multiple channels, and
   each of the ridges of the second processing component forms a gap with the second surface of the processing component such that the gap is smaller than the diameter of at least one of the cells thereby causing compression of the at least one of the cells while the cells pass through the gap.

4. The cell processing apparatus of claim 1, wherein the first surface of the processing component directly contacts the outlet plate.

5. The cell processing apparatus of claim 1, wherein the channels of the processing component extend parallel to each other.

6. The cell processing apparatus of claim 1, wherein the channels of the processing component extend perpendicular to the inlet opening and the outlet opening.

7. The cell processing apparatus of claim 1, wherein at least one of the inlet plate and the outlet plate is integrated with the processing component.

8. The cell processing apparatus of claim 1, wherein each of the inlet plate and the outlet plate is sealed against the processing component.

9. The cell processing apparatus of claim 1, wherein each of the inlet opening and the outlet opening has a cross-sectional area that changes along a direction perpendicular to the channels of the processing component.

10. The cell processing apparatus of claim 1, wherein the ridges are oriented at an angle (a) between 30 degrees to 90 degrees relative to a central flow axis in each of the channels.

11. The cell processing apparatus of claim 1, wherein:
    the processing component is operable as a separator for separating the cells from the cell media;
    the ridges are configured to direct the cells in the combination of the cell media and the cells to the outlet opening of the outlet plate; and
    the outlet plate comprises a second outlet opening for removing the cell media from the processing component.

12. The cell processing apparatus of claim 1, wherein:
    the inlet plate is configured to connect to a sterile bag operable as a cell media source; and
    the outlet plate is configured to connect to an additional sterile bag operable as a cell media receiver.

13. The cell processing apparatus of claim 1, wherein the inlet plate comprises a collector port fluidically coupled to each of the multiple channels and configured to connect to a gas flow source.

14. The cell processing apparatus of claim 1, wherein the inlet opening is positioned at a top of the cell processing apparatus thereby reducing air bubbles in the combination of the cell media and the cells through the inlet opening.

15. The cell processing apparatus of claim 1, wherein the inlet plate or the processing component comprises a distribution pathway fluidically coupled to each of the channels in the processing component.

16. The cell processing apparatus of claim 1, wherein at least a portion of the processing component is formed from silicon.

17. The cell processing apparatus of claim 1, wherein at least a portion of the processing component is formed from glass.

18. The cell processing apparatus of claim 1, wherein the inlet opening comprises a level sensor for measuring a level of the combination of the cell media and the cells within the inlet opening.

19. The cell processing apparatus of claim 1, wherein the inlet opening comprises a pressure sensor for measuring pressure within the inlet opening.

20. The cell processing apparatus of claim 1, wherein the processing component is operable as one or more of a primary filter, a mechanoporator, or a separator.

* * * * *